United States Patent
Murray et al.

(10) Patent No.: US 12,414,797 B2
(45) Date of Patent: Sep. 16, 2025

(54) PUNCTURE NEEDLES

(71) Applicant: Edwards Lifesciences Corporation, Irvine, CA (US)

(72) Inventors: Daniel James Murray, Orange, CA (US); Lillian Grace Myers, Prairie Village, KS (US); Don Huy Tran, Westminster, CA (US); Michael G. Valdez, Riverside, CA (US); Andrew Charles May, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 568 days.

(21) Appl. No.: 17/676,049

(22) Filed: Feb. 18, 2022

(65) Prior Publication Data

US 2022/0168015 A1 Jun. 2, 2022

Related U.S. Application Data

(63) Continuation of application No. PCT/US2020/045713, filed on Aug. 11, 2020.
(Continued)

(51) Int. Cl.
*A61B 17/34* (2006.01)
*A61M 25/00* (2006.01)
(Continued)

(52) U.S. Cl.
CPC ..... *A61B 17/3468* (2013.01); *A61M 25/0082* (2013.01); *A61M 2025/0095* (2013.01)

(58) Field of Classification Search
CPC ............ A61B 17/3468; A61B 17/3478; A61B 2017/320044; A61B 2017/320077;
(Continued)

(56) References Cited

U.S. PATENT DOCUMENTS 3,538,917 A  11/1970 Selker
3,675,656 A   7/1972 Hakim
(Continued)

FOREIGN PATENT DOCUMENTS

EP    1962720 A2    9/2008
WO    2011089014 A1   7/2011
(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.
(Continued)

*Primary Examiner* — Tan-Uyen T Ho
*Assistant Examiner* — Lindsey R. Rivers
(74) *Attorney, Agent, or Firm* — Chang & Hale LLP

(57) ABSTRACT

A puncture needle can comprise an elongate portion, a puncture component associated with a distal end of the elongate portion, and a spacer associated with a distal portion of the elongate portion, where the spacer can be configured to contact a wall of the delivery catheter lumen to prevent contact between the puncture component and the wall. A puncture needle can comprise an elongate portion and a puncture component associated with a distal end of the elongate portion, where the puncture component comprises a blade edge on a distal edge, and where the puncture component is configured to be advanceable through a lumen of a delivery catheter without the blade edge sticking to a wall of the lumen.

11 Claims, 20 Drawing Sheets

Related U.S. Application Data

(60) Provisional application No. 62/890,528, filed on Aug. 22, 2019.

(51) Int. Cl.

| | |
|---|---|
| A61B 17/00 | (2006.01) |
| A61B 17/3209 | (2006.01) |
| A61B 90/00 | (2016.01) |
| A61M 25/06 | (2006.01) |

(58) Field of Classification Search
CPC .. A61B 2017/320082; A61M 25/0082; A61M 2025/0095
See application file for complete search history.

(56) References Cited

U.S. PATENT DOCUMENTS

| | | | |
|---|---|---|---|
| 3,730,186 A | 5/1973 | Edmunds, Jr. et al. |
| 3,853,126 A | 12/1974 | Schulte |
| 3,882,862 A | 5/1975 | Berend |
| 3,882,882 A | 5/1975 | Preisig |
| 3,903,894 A | 9/1975 | Rosen et al. |
| 4,256,094 A | 3/1981 | Kapp et al. |
| 4,428,365 A | 1/1984 | Hakky |
| 4,556,050 A | 12/1985 | Hodgson et al. |
| 4,578,061 A | 3/1986 | Lemelson |
| 4,586,501 A | 5/1986 | Claracq |
| 4,601,718 A | 7/1986 | Possis et al. |
| 4,655,777 A | 4/1987 | Dunn et al. |
| 4,708,140 A | 11/1987 | Baron |
| 4,712,551 A | 12/1987 | Rayhanabad |
| 4,739,762 A | 4/1988 | Palmaz |
| 4,762,128 A | 8/1988 | Rosenbluth |
| 4,774,949 A | 10/1988 | Fogarty |
| 4,828,544 A | 5/1989 | Lane et al. |
| 4,861,336 A | 8/1989 | Helzel |
| 4,881,939 A | 11/1989 | Newman |
| 4,946,457 A | 8/1990 | Elliott |
| 4,950,227 A | 8/1990 | Savin et al. |
| 4,961,729 A | 10/1990 | Vaillancourt |
| 4,997,431 A | 3/1991 | Isner et al. |
| 5,026,377 A | 6/1991 | Burton et al. |
| 5,054,492 A | 10/1991 | Scribner et al. |
| 5,108,420 A | 4/1992 | Marks |
| 5,109,420 A | 4/1992 | Nonaka |
| 5,167,239 A | 12/1992 | Cohen et al. |
| 5,190,528 A | 3/1993 | Fonger et al. |
| 5,193,546 A | 3/1993 | Shaknovich |
| 5,201,757 A | 4/1993 | Heyn et al. |
| 5,242,397 A | 9/1993 | Barath et al. |
| 5,242,410 A | 9/1993 | Melker |
| 5,258,042 A | 11/1993 | Mehta |
| 5,267,940 A | 12/1993 | Moulder |
| 5,287,861 A | 2/1994 | Wilk |
| 5,330,496 A | 7/1994 | Alferness |
| 5,334,217 A | 8/1994 | Das |
| 5,345,940 A | 9/1994 | Seward et al. |
| 5,354,279 A | 10/1994 | Hofling |
| 5,366,490 A | 11/1994 | Edwards et al. |
| 5,373,849 A | 12/1994 | Maroney et al. |
| 5,419,777 A | 5/1995 | Hofling |
| 5,423,878 A | 6/1995 | Franz |
| 5,429,634 A | 7/1995 | Narciso, Jr. |
| 5,431,700 A | 7/1995 | Sloan |
| 5,443,497 A | 8/1995 | Venbrux |
| 5,445,600 A | 8/1995 | Abdulla |
| 5,445,646 A | 8/1995 | Euteneuer et al. |
| 5,456,284 A | 10/1995 | Ryan et al. |
| 5,456,712 A | 10/1995 | Maginot |
| 5,462,523 A | 10/1995 | Samson et al. |
| 5,464,395 A | 11/1995 | Faxon et al. |
| 5,491,224 A | 2/1996 | Bittner et al. |
| 5,496,311 A | 3/1996 | Abele et al. |
| 5,499,630 A | 3/1996 | Hiki et al. |
| 5,507,724 A | 4/1996 | Hofmann et al. |
| 5,507,725 A | 4/1996 | Savage et al. |
| 5,538,504 A | 7/1996 | Linden et al. |
| 5,551,954 A | 9/1996 | Buscemi et al. |
| 5,554,182 A | 9/1996 | Dinh et al. |
| 5,570,693 A | 11/1996 | Jang et al. |
| 5,571,086 A | 11/1996 | Kaplan et al. |
| 5,571,151 A | 11/1996 | Gregory |
| 5,588,960 A | 12/1996 | Edwards et al. |
| 5,597,378 A | 1/1997 | Jervis |
| 5,599,300 A | 2/1997 | Weaver et al. |
| 5,614,204 A | 3/1997 | Cochrum |
| 5,628,784 A | 5/1997 | Strecker |
| 5,661,133 A | 8/1997 | Leiden et al. |
| 5,662,609 A | 9/1997 | Slepian |
| 5,662,711 A | 9/1997 | Douglas |
| 5,665,077 A | 9/1997 | Rosen et al. |
| 5,669,880 A | 9/1997 | Solar |
| 5,682,906 A | 11/1997 | Sterman et al. |
| 5,690,670 A | 11/1997 | Davidson |
| 5,693,029 A | 12/1997 | Leonhardt |
| 5,704,361 A | 1/1998 | Seward et al. |
| 5,704,926 A | 1/1998 | Sutton |
| 5,713,363 A | 2/1998 | Seward et al. |
| 5,713,853 A | 2/1998 | Clark et al. |
| 5,718,725 A | 2/1998 | Sterman et al. |
| 5,724,975 A | 3/1998 | Negus et al. |
| 5,724,977 A | 3/1998 | Yock et al. |
| 5,728,123 A | 3/1998 | Lemelson et al. |
| 5,735,847 A | 4/1998 | Gough et al. |
| 5,738,658 A | 4/1998 | Maus et al. |
| 5,743,874 A | 4/1998 | Fischell et al. |
| 5,755,682 A | 5/1998 | Knudson et al. |
| 5,756,696 A | 5/1998 | Gray et al. |
| 5,771,895 A | 6/1998 | Slager |
| 5,772,629 A | 6/1998 | Kaplan |
| 5,772,632 A | 6/1998 | Forman |
| 5,807,258 A | 9/1998 | Cimochowski et al. |
| 5,807,306 A | 9/1998 | Shapland et al. |
| 5,810,780 A | 9/1998 | Brimhall et al. |
| 5,814,005 A | 9/1998 | Barra et al. |
| 5,827,216 A | 10/1998 | Igo et al. |
| 5,830,222 A | 11/1998 | Makower |
| 5,830,224 A | 11/1998 | Cohn et al. |
| 5,836,913 A | 11/1998 | Orth et al. |
| 5,843,090 A | 12/1998 | Schuetz |
| 5,843,170 A | 12/1998 | Ahn |
| 5,944,738 A | 8/1999 | Amplatz et al. |
| 5,951,569 A | 9/1999 | Tuckey et al. |
| 5,989,280 A | 11/1999 | Euteneuer et al. |
| 6,019,788 A | 2/2000 | Butters et al. |
| 6,042,589 A | 3/2000 | Marianne |
| 6,053,891 A | 4/2000 | DeCampli |
| 6,081,738 A | 6/2000 | Hinohara et al. |
| 6,086,553 A | 7/2000 | Akbik |
| 6,092,526 A | 7/2000 | LaFontaine et al. |
| 6,095,878 A | 8/2000 | Van Balen |
| 6,113,612 A | 9/2000 | Swanson et al. |
| 6,120,494 A | 9/2000 | Jonkman |
| 6,120,522 A | 9/2000 | Vrba et al. |
| 6,120,534 A | 9/2000 | Ruiz |
| 6,152,937 A | 11/2000 | Peterson et al. |
| 6,165,185 A | 12/2000 | Shennib et al. |
| 6,168,620 B1 | 1/2001 | Kerr |
| 6,168,820 B1 | 1/2001 | Garwood et al. |
| 6,174,681 B1 | 1/2001 | Halling et al. |
| 6,190,353 B1 | 2/2001 | Makower et al. |
| 6,193,734 B1 | 2/2001 | Bolduc et al. |
| 6,196,230 B1 | 3/2001 | Hall et al. |
| 6,241,743 B1 | 6/2001 | Levin et al. |
| 6,248,117 B1 | 6/2001 | Blatter |
| 6,251,116 B1 | 6/2001 | Shennib et al. |
| 6,254,631 B1 | 7/2001 | Thompson |
| 6,280,412 B1 | 8/2001 | Pederson, Jr. et al. |
| 6,283,951 B1 | 9/2001 | Flaherty et al. |
| 6,287,332 B1 | 9/2001 | Bolz et al. |
| 6,290,728 B1 | 9/2001 | Phelps et al. |
| 6,302,875 B1 | 10/2001 | Makower et al. |
| 6,302,892 B1 | 10/2001 | Wilk |

(56) References Cited

U.S. PATENT DOCUMENTS

| | | | |
|---|---|---|---|
| 6,302,905 B1 | 10/2001 | Goldsteen et al. |
| 6,309,415 B1 | 10/2001 | Pulnev et al. |
| 6,315,752 B1 | 11/2001 | DiMatteo |
| 6,325,798 B1 | 12/2001 | Edwards et al. |
| 6,361,545 B1 | 3/2002 | Macoviak et al. |
| 6,375,615 B1 | 4/2002 | Flaherty et al. |
| 6,387,116 B1 | 5/2002 | McKenzie et al. |
| 6,387,119 B2 | 5/2002 | Wolf et al. |
| 6,391,036 B1 | 5/2002 | Berg et al. |
| 6,402,767 B1 | 6/2002 | Nash et al. |
| 6,443,158 B1 | 9/2002 | LaFontaine et al. |
| 6,451,048 B1 | 9/2002 | Berg et al. |
| 6,458,140 B2 | 10/2002 | Akin et al. |
| 6,464,665 B1 | 10/2002 | Heuser |
| 6,468,303 B1 | 10/2002 | Amplatz et al. |
| 6,475,226 B1 | 11/2002 | Belef et al. |
| 6,494,889 B1 | 12/2002 | Fleischman et al. |
| 6,503,247 B2 | 1/2003 | Swartz et al. |
| 6,506,201 B2 | 1/2003 | Di Caprio et al. |
| 6,508,824 B1 | 1/2003 | Flaherty et al. |
| 6,561,998 B1 | 5/2003 | Roth et al. |
| 6,562,066 B1 | 5/2003 | Martin |
| 6,565,542 B2 | 5/2003 | Kumar et al. |
| 6,575,168 B2 | 6/2003 | LaFontaine et al. |
| 6,579,311 B1 | 6/2003 | Makower |
| 6,589,251 B2 | 7/2003 | Yee et al. |
| 6,595,941 B1 | 7/2003 | Blatter |
| 6,602,241 B2 | 8/2003 | Makower et al. |
| 6,613,074 B1 | 9/2003 | Mitelberg et al. |
| 6,616,624 B1 | 9/2003 | Kieval |
| 6,616,675 B1 | 9/2003 | Evard et al. |
| 6,620,202 B2 | 9/2003 | Bottcher et al. |
| 6,623,494 B1 | 9/2003 | Blatter |
| 6,626,920 B2 | 9/2003 | Whayne |
| 6,638,293 B1 | 10/2003 | Makower et al. |
| 6,692,482 B2 | 2/2004 | Heller et al. |
| 6,695,878 B2 | 2/2004 | McGuckin, Jr. et al. |
| 6,699,256 B1 | 3/2004 | Logan et al. |
| 6,702,828 B2 | 3/2004 | Whayne |
| 6,709,414 B2 | 3/2004 | Weitzel et al. |
| 6,709,444 B1 | 3/2004 | Makower |
| 6,712,836 B1 | 3/2004 | Berg et al. |
| 6,719,804 B2 | 4/2004 | St. Pierre |
| 6,726,659 B1 | 4/2004 | Stocking et al. |
| 6,726,677 B1 | 4/2004 | Flaherty et al. |
| 6,736,825 B2 | 5/2004 | Blatter et al. |
| 6,740,426 B2 | 5/2004 | Kawachi et al. |
| 6,743,244 B2 | 6/2004 | Blatter et al. |
| 6,743,259 B2 | 6/2004 | Ginn |
| 6,746,426 B1 | 6/2004 | Flaherty et al. |
| 6,748,484 B1 | 6/2004 | Henderson et al. |
| 6,758,854 B1 | 7/2004 | Butler et al. |
| 6,776,785 B1 | 8/2004 | Yencho et al. |
| 6,797,083 B2 | 9/2004 | Peterson |
| 6,802,858 B2 | 10/2004 | Gambale et al. |
| 6,805,706 B2 | 10/2004 | Solovay et al. |
| 6,808,498 B2 | 10/2004 | Laroya et al. |
| 6,827,698 B1 | 12/2004 | Kleinekofort |
| 6,847,348 B2 | 1/2005 | Rojewski |
| 6,854,172 B2 | 2/2005 | Kaese et al. |
| 6,858,035 B2 | 2/2005 | Whayne |
| 6,869,437 B1 | 3/2005 | Hausen et al. |
| 6,893,413 B2 | 5/2005 | Martin |
| 6,913,600 B2 | 7/2005 | Valley et al. |
| 6,913,607 B2 | 7/2005 | Ainsworth et al. |
| 6,915,154 B1 | 7/2005 | Docherty et al. |
| 6,926,690 B2 | 8/2005 | Renati |
| 6,972,023 B2 | 12/2005 | Whayne et al. |
| 6,979,351 B2 | 12/2005 | Forsell et al. |
| 6,985,774 B2 | 1/2006 | Kieval et al. |
| 7,002,491 B2 | 2/2006 | Robbins |
| 7,008,397 B2 | 3/2006 | Tweden et al. |
| 7,011,094 B2 | 3/2006 | Rapacki et al. |
| 7,011,678 B2 | 3/2006 | Tenerz et al. |
| 7,025,741 B2 | 4/2006 | Cull |
| 7,025,746 B2 | 4/2006 | Tal |
| 7,037,329 B2 | 5/2006 | Martin |
| 7,056,294 B2 | 6/2006 | Khairkhahan et al. |
| 7,056,320 B2 | 6/2006 | Utley et al. |
| 7,056,325 B1 | 6/2006 | Makower et al. |
| 7,077,860 B2 | 7/2006 | Yan et al. |
| 7,083,631 B2 | 8/2006 | Houser et al. |
| 7,108,701 B2 | 9/2006 | Evens et al. |
| 7,115,136 B2 | 10/2006 | Park et al. |
| 7,118,546 B2 | 10/2006 | Blatter |
| 7,128,750 B1 | 10/2006 | Stergiopulos |
| 7,175,644 B2 | 2/2007 | Cooper et al. |
| 7,182,771 B1 | 2/2007 | Houser et al. |
| 7,235,095 B2 | 6/2007 | Haverkost et al. |
| 7,294,115 B1 | 11/2007 | Wilk |
| 7,316,706 B2 | 1/2008 | Bloom et al. |
| 7,317,951 B2 | 1/2008 | Schneider et al. |
| 7,318,804 B2 | 1/2008 | Weitzel et al. |
| 7,326,221 B2 | 2/2008 | Sakamoto et al. |
| 7,331,985 B2 | 2/2008 | Thompson et al. |
| 7,335,220 B2 | 2/2008 | Khosravi et al. |
| 7,351,247 B2 | 4/2008 | Kupiecki et al. |
| 7,361,181 B2 | 4/2008 | Hindrichs et al. |
| 7,374,567 B2 | 5/2008 | Heuser |
| D581,054 S | 11/2008 | Moore |
| 7,462,162 B2 | 12/2008 | Phan et al. |
| 7,476,200 B2 | 1/2009 | Tal |
| 7,530,963 B2 | 5/2009 | Albright |
| 7,563,277 B2 | 7/2009 | Case et al. |
| 7,623,926 B2 | 11/2009 | Rossing et al. |
| 7,625,593 B2 | 12/2009 | Mandrusov et al. |
| 7,628,768 B2 | 12/2009 | Faul et al. |
| D612,499 S | 3/2010 | Ondracek et al. |
| 7,691,110 B2 | 4/2010 | Secrest et al. |
| 7,699,863 B2 | 4/2010 | Marco et al. |
| 7,722,549 B2 | 5/2010 | Nakao |
| 7,722,665 B2 | 5/2010 | Anwar et al. |
| 7,744,621 B2 | 6/2010 | Paul et al. |
| 7,794,495 B2 | 9/2010 | Gale et al. |
| 7,807,191 B2 | 10/2010 | Iyer et al. |
| 7,815,590 B2 | 10/2010 | Cooper |
| 7,815,656 B2 | 10/2010 | Rust et al. |
| 7,815,852 B2 | 10/2010 | Sternby |
| 7,828,814 B2 | 11/2010 | Brenneman et al. |
| 7,846,179 B2 | 12/2010 | Belef et al. |
| 7,846,194 B2 | 12/2010 | Hartley et al. |
| 7,850,705 B2 | 12/2010 | Bachinski et al. |
| 7,867,547 B2 | 1/2011 | Tochterman et al. |
| 7,879,367 B2 | 2/2011 | Heublein et al. |
| 7,892,246 B2 | 2/2011 | Akin et al. |
| 7,892,247 B2 | 2/2011 | Conston et al. |
| 7,923,022 B2 | 4/2011 | Wang et al. |
| 7,951,194 B2 | 5/2011 | Gueriguian et al. |
| 7,959,603 B2 | 6/2011 | Wahr et al. |
| 7,964,210 B2 | 6/2011 | Wang et al. |
| 7,967,769 B2 | 6/2011 | Faul et al. |
| 7,972,346 B2 | 7/2011 | Bachmann et al. |
| 8,002,821 B2 | 8/2011 | Stinson |
| 8,016,782 B2 | 9/2011 | Brenneman et al. |
| 8,029,470 B2 | 10/2011 | Whiting et al. |
| 8,048,150 B2 | 11/2011 | Weber et al. |
| 8,052,751 B2 | 11/2011 | Aklog et al. |
| 8,057,534 B2 | 11/2011 | Boismier et al. |
| 8,070,708 B2 | 12/2011 | Rottenberg et al. |
| 8,088,171 B2 | 1/2012 | Brenneman |
| 8,089,029 B2 | 1/2012 | Flanagan |
| 8,091,556 B2 | 1/2012 | Keren et al. |
| 8,128,689 B2 | 3/2012 | Weber et al. |
| 8,152,773 B2 | 4/2012 | Albrecht et al. |
| 8,182,527 B2 | 5/2012 | Llanos et al. |
| 8,214,015 B2 | 7/2012 | Macaulay et al. |
| 8,221,495 B2 | 7/2012 | Shrivastava et al. |
| 8,226,592 B2 | 7/2012 | Brenneman et al. |
| D665,500 S | 8/2012 | Martin et al. |
| 8,282,591 B2 | 10/2012 | Khan et al. |
| 8,292,910 B2 * | 10/2012 | Chanduszko ...... A61B 17/0057 606/213 |
| 8,308,682 B2 | 11/2012 | Kramer et al. |
| 8,357,193 B2 | 1/2013 | Phan et al. |

(56) References Cited

U.S. PATENT DOCUMENTS

| | | |
|---|---|---|
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,276 B2 | 2/2015 | Kellerman et al. |
| 9,005,155 B2 | 4/2015 | Sugimoto |
| 9,044,588 B2 | 6/2015 | Conn |
| 9,061,115 B2 | 6/2015 | Ward et al. |
| 9,067,050 B2 | 6/2015 | Gallagher et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,789,294 B2 | 10/2017 | Taft et al. |
| 9,814,483 B2 | 11/2017 | Vardi |
| 9,827,404 B2 | 11/2017 | Nance et al. |
| 9,839,517 B2 | 12/2017 | Centola et al. |
| 9,848,900 B2 * | 12/2017 | Witt .............. A61B 17/320068 |
| 9,872,981 B2 | 1/2018 | Sparks et al. |
| 9,943,665 B2 | 4/2018 | Valeti et al. |
| 9,980,815 B2 | 5/2018 | Nitzan et al. |
| 10,076,403 B1 | 9/2018 | Eigler et al. |
| 10,130,371 B2 | 11/2018 | Dehdashtian et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,234,702 B2 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 11,395,644 B2 | 7/2022 | Alanbaei |
| 11,420,034 B2 | 8/2022 | Solomon et al. |
| 2001/0000041 A1 | 3/2001 | Selmon et al. |
| 2001/0025643 A1 | 10/2001 | Foley |
| 2001/0045698 A1 | 11/2001 | Lo |
| 2002/0013616 A1 | 1/2002 | Carter et al. |
| 2002/0029079 A1 | 3/2002 | Kim et al. |
| 2002/0062146 A1 | 5/2002 | Makower et al. |
| 2002/0169466 A1 | 11/2002 | Peterson et al. |
| 2002/0193751 A1 | 12/2002 | Theeuwes et al. |
| 2002/0198501 A1 | 12/2002 | Kumar et al. |
| 2003/0017150 A1 | 1/2003 | Torphy |
| 2003/0060876 A1 | 3/2003 | Loshakove et al. |
| 2003/0065345 A1 | 4/2003 | Weadock |
| 2003/0181928 A1 | 9/2003 | Vidlund et al. |
| 2003/0225425 A1 | 12/2003 | Kupiecki et al. |
| 2004/0064081 A1 | 4/2004 | Stanish |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0230156 A1 | 11/2004 | Schreck et al. |
| 2004/0260318 A1 | 12/2004 | Hunter et al. |
| 2005/0021085 A1 | 1/2005 | Abrams et al. |
| 2005/0038501 A1 | 2/2005 | Moore et al. |
| 2005/0043708 A1 | 2/2005 | Gleeson et al. |
| 2005/0049675 A1 | 3/2005 | Wallace |
| 2005/0060041 A1 | 3/2005 | Phan et al. |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0149096 A1 | 7/2005 | Hilal et al. |
| 2005/0165344 A1 | 7/2005 | Dobak |
| 2005/0228402 A1 | 10/2005 | Hofmann |
| 2005/0249770 A1 | 11/2005 | Hunter |
| 2005/0249776 A1 | 11/2005 | Chen et al. |
| 2005/0272806 A1 | 12/2005 | Falotico et al. |
| 2006/0024359 A1 | 2/2006 | Walker et al. |
| 2006/0034466 A1 | 2/2006 | Form et al. |
| 2006/0074398 A1 | 4/2006 | Whiting et al. |
| 2006/0111704 A1 | 5/2006 | Brenneman et al. |
| 2006/0130591 A1 | 6/2006 | Perkins |
| 2006/0130767 A1 | 6/2006 | Herchen |
| 2006/0173440 A1 * | 8/2006 | Lamson .............. A61M 5/3291 604/506 |
| 2006/0182536 A1 | 8/2006 | Rice et al. |
| 2006/0198869 A1 | 9/2006 | Furst et al. |
| 2006/0241342 A1 | 10/2006 | Macaulay et al. |
| 2006/0264801 A1 | 11/2006 | Bolling et al. |
| 2006/0271196 A1 | 11/2006 | Saal et al. |
| 2006/0293701 A1 | 12/2006 | Ainsworth et al. |
| 2007/0083258 A1 | 4/2007 | Falotico et al. |
| 2007/0173787 A1 | 7/2007 | Huang et al. |
| 2007/0179426 A1 | 8/2007 | Selden |
| 2007/0213750 A1 | 9/2007 | Weadock |
| 2008/0021485 A1 | 1/2008 | Catanese et al. |
| 2008/0051883 A1 | 2/2008 | Llanos et al. |
| 2008/0091264 A1 | 4/2008 | Machold et al. |
| 2008/0109069 A1 | 5/2008 | Coleman et al. |
| 2008/0161904 A1 | 7/2008 | Heuser et al. |
| 2008/0167595 A1 | 7/2008 | Porter et al. |
| 2008/0234842 A1 | 9/2008 | Zhang |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0187116 A1 | 7/2009 | Noishiki et al. |
| 2009/0281379 A1 | 11/2009 | Binmoeller et al. |
| 2010/0030321 A1 | 2/2010 | Mach |
| 2010/0106171 A1 | 4/2010 | Arepally et al. |
| 2010/0198041 A1 | 8/2010 | Christian et al. |
| 2010/0217382 A1 | 8/2010 | Chau et al. |
| 2010/0298930 A1 | 11/2010 | Orlov |
| 2011/0096036 A1 | 4/2011 | McIntosh et al. |
| 2011/0106118 A1 | 5/2011 | Son et al. |
| 2011/0251482 A1 | 10/2011 | Kellerman et al. |
| 2012/0041544 A1 | 2/2012 | Wolf |
| 2012/0053686 A1 | 3/2012 | McNamara et al. |
| 2012/0143141 A1 | 6/2012 | Verkaik et al. |
| 2012/0265229 A1 | 10/2012 | Rottenberg et al. |
| 2013/0022214 A1 | 1/2013 | Dickins et al. |

(56) References Cited

U.S. PATENT DOCUMENTS

| | | |
|---|---|---|
| 2013/0030521 A1 | 1/2013 | Nitzan et al. |
| 2013/0178784 A1 | 7/2013 | McNamara et al. |
| 2013/0253342 A1 | 9/2013 | Griswold et al. |
| 2013/0281988 A1 | 10/2013 | Magnin et al. |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2015/0119796 A1 | 4/2015 | Finch |
| 2015/0148731 A1 | 5/2015 | McNamara et al. |
| 2015/0151101 A1 | 6/2015 | Bonnette et al. |
| 2015/0238729 A1 | 8/2015 | Jenson et al. |
| 2016/0022293 A1 | 1/2016 | Dubrul et al. |
| 2016/0022970 A1 | 1/2016 | Forcucci et al. |
| 2016/0058452 A1 | 3/2016 | Brenneman et al. |
| 2016/0120550 A1 | 5/2016 | McNamara et al. |
| 2016/0220357 A1 | 8/2016 | Anand et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2016/0338734 A1* | 11/2016 | Shah .................. A61B 5/14532 |
| 2017/0090865 A1 | 3/2017 | Armstrong-Muntner et al. |
| 2017/0113026 A1 | 4/2017 | Finch |
| 2017/0128705 A1 | 5/2017 | Forcucci et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0177516 A1 | 6/2018 | Vardi et al. |
| 2018/0339131 A1* | 11/2018 | Muse .................. A61M 25/0102 |
| 2019/0008628 A1 | 1/2019 | Eigler et al. |
| 2019/0269392 A1 | 9/2019 | Celermajer et al. |
| 2019/0298909 A1 | 10/2019 | Cully et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0045691 A1 | 2/2021 | Zou et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0121179 A1 | 4/2021 | Ben-David et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0236138 A1 | 8/2021 | Perszyk et al. |
| 2021/0290214 A1 | 9/2021 | Cole et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0096087 A1 | 3/2022 | Valdez |
| 2022/0110679 A1 | 4/2022 | Wang et al. |
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | McNamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0263949 A1 | 8/2023 | Passman et al. |
| 2023/0285133 A1 | 9/2023 | Eigler et al. |
| 2023/0330398 A1 | 10/2023 | Nae et al. |

FOREIGN PATENT DOCUMENTS

| | | |
|---|---|---|
| WO | 2018083599 A1 | 5/2018 |
| WO | 2020215090 A1 | 10/2020 |
| WO | 2021091566 A1 | 5/2021 |
| WO | 2022031317 A1 | 2/2022 |
| WO | 2022060630 A1 | 3/2022 |
| WO | 2022133070 A1 | 6/2022 |
| WO | 2022169865 A1 | 8/2022 |
| WO | 2022177737 A1 | 8/2022 |
| WO | 2022197454 A1 | 9/2022 |
| WO | 2022197455 A1 | 9/2022 |
| WO | 2022232133 A1 | 11/2022 |
| WO | 2022246158 A1 | 11/2022 |
| WO | 2022246166 A1 | 11/2022 |
| WO | 2022271473 A1 | 12/2022 |
| WO | 2023022883 A1 | 2/2023 |
| WO | 2023027926 A1 | 3/2023 |
| WO | 2023079498 A1 | 5/2023 |
| WO | 2023081127 A1 | 5/2023 |
| WO | 2023081129 A1 | 5/2023 |
| WO | 2023154235 A1 | 8/2023 |
| WO | 2023154308 A1 | 8/2023 |
| WO | 2023172435 A1 | 9/2023 |
| WO | 2023172436 A1 | 9/2023 |
| WO | 2023196243 A1 | 10/2023 |
| WO | 2023239784 A1 | 12/2023 |
| WO | 2023239785 A1 | 12/2023 |
| WO | 2023239788 A2 | 12/2023 |

OTHER PUBLICATIONS

Kong, et al.—Creation of an Intra-atrial Communication With a New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, pp. 398401.

Ruebben et al., "Arteriovenous fistulas induced by femoral arterial catheterization: percuntaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

\* cited by examiner

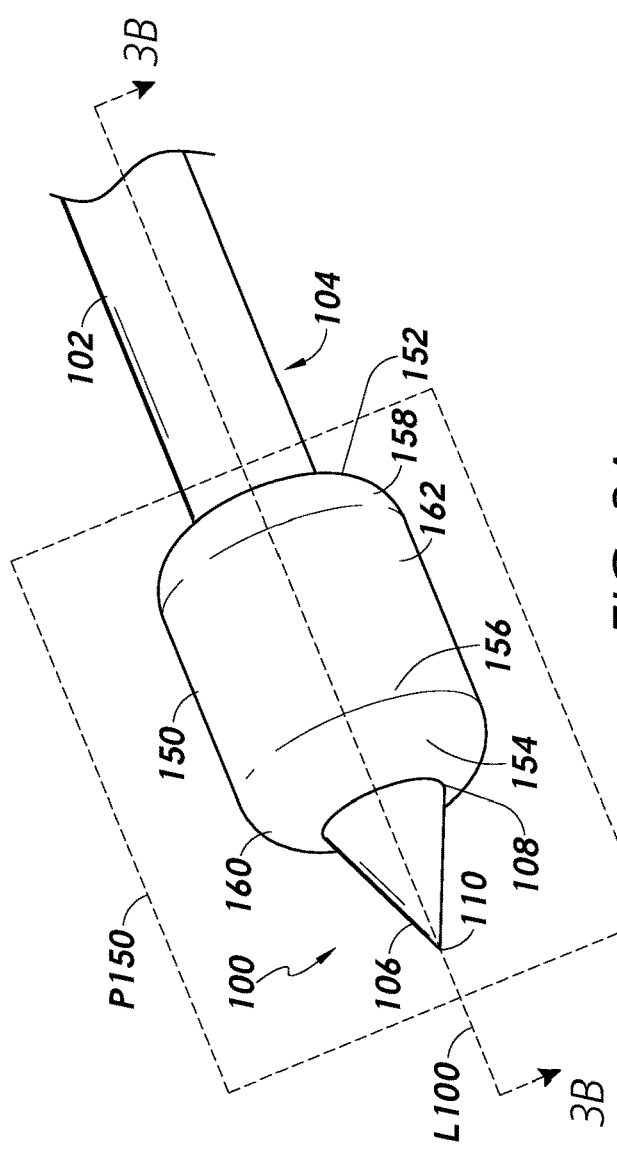
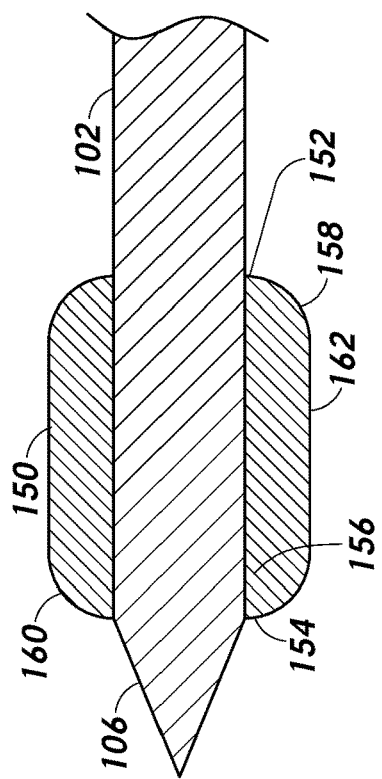
FIG. 3A
FIG. 3B

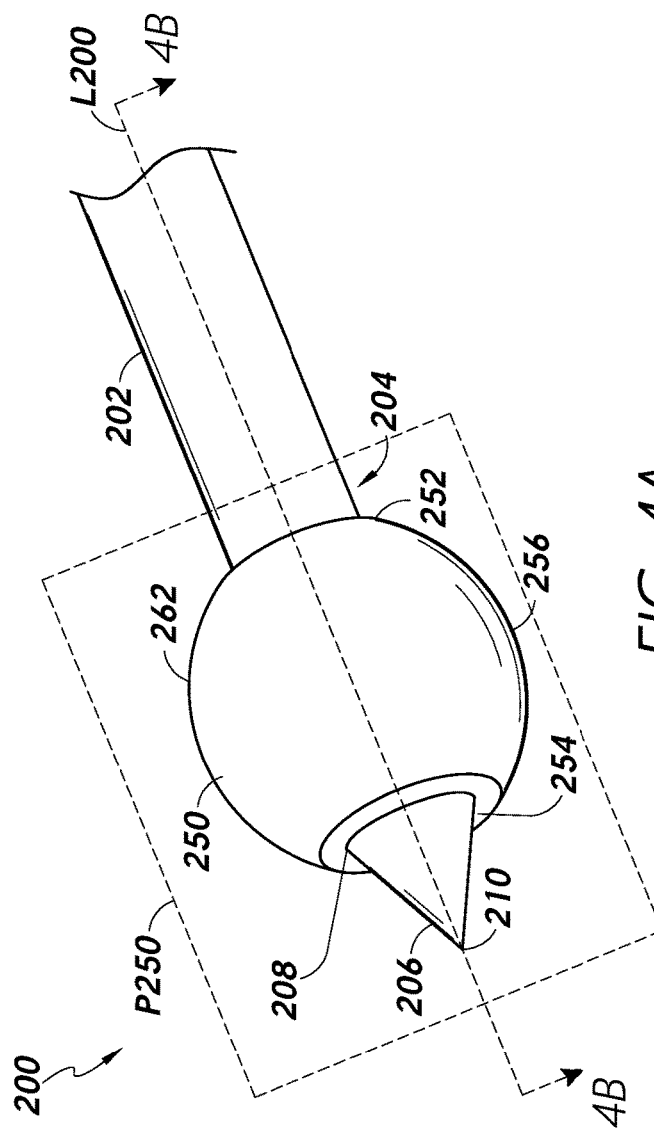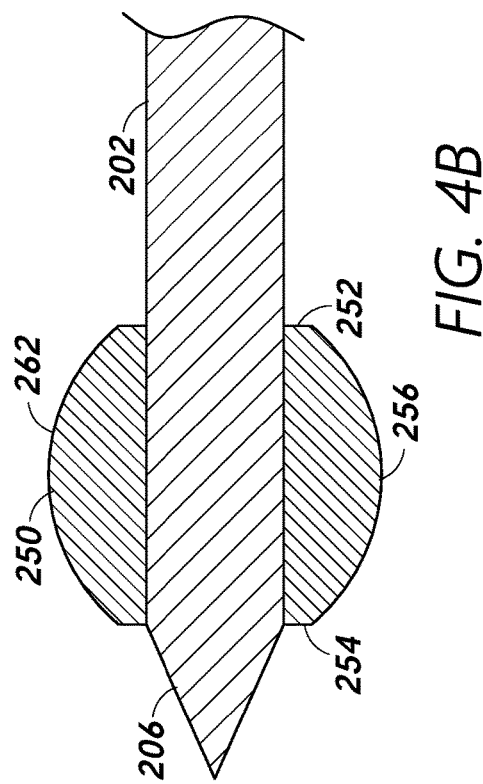

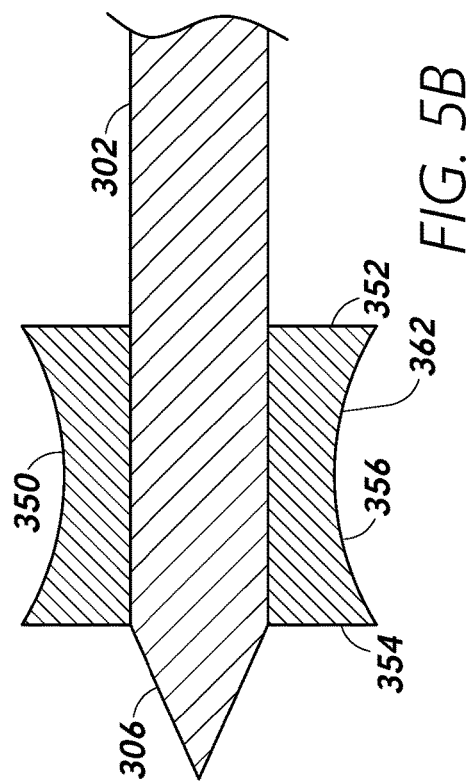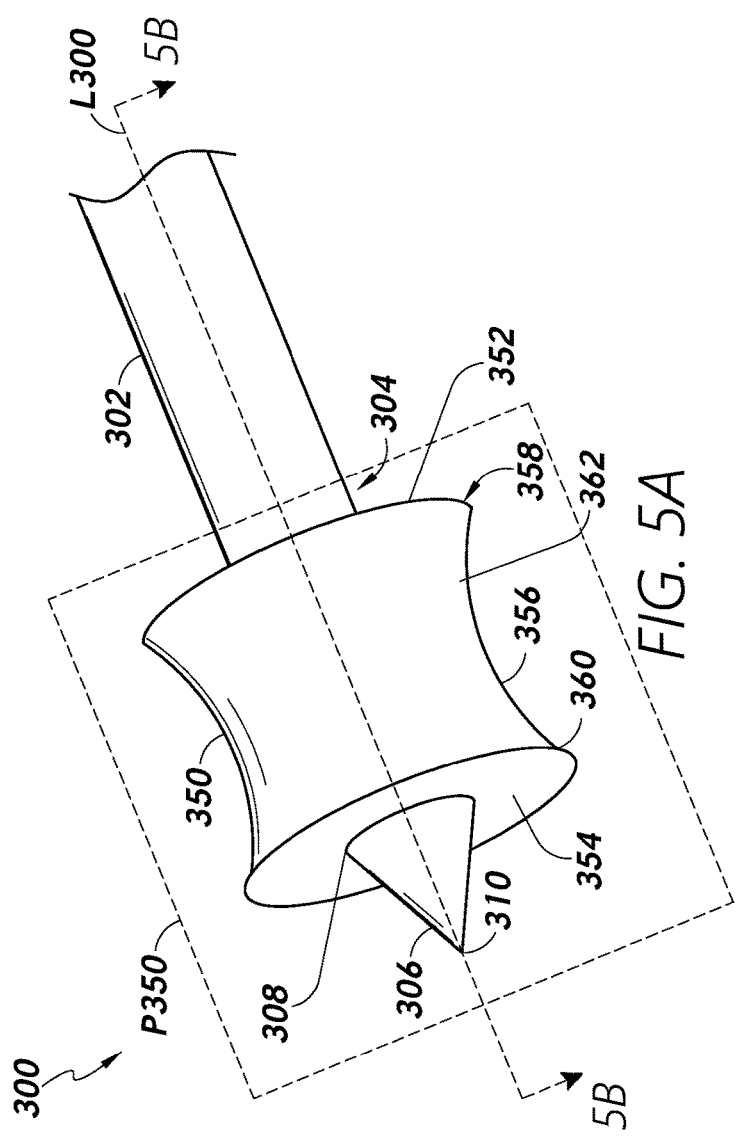

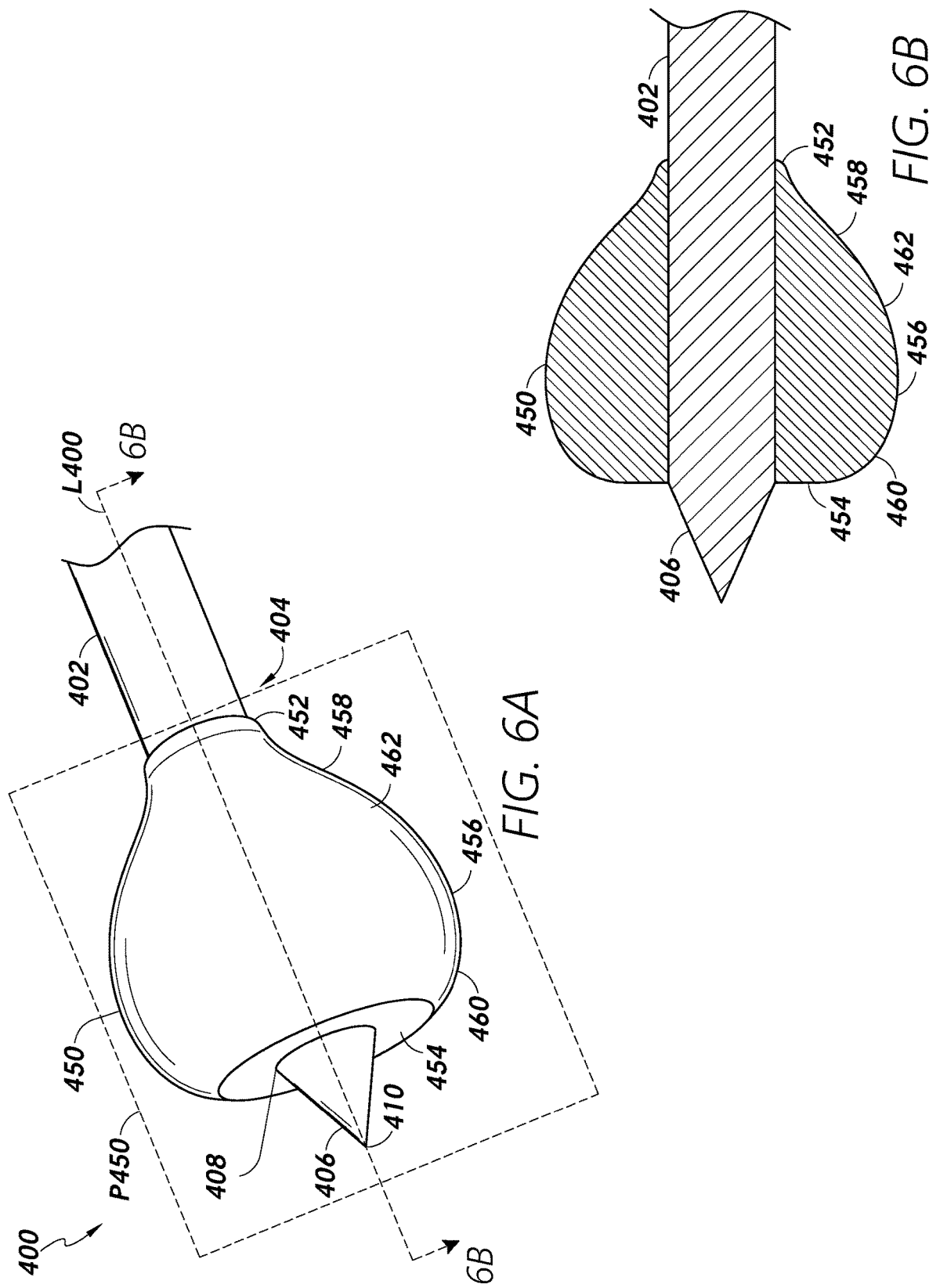

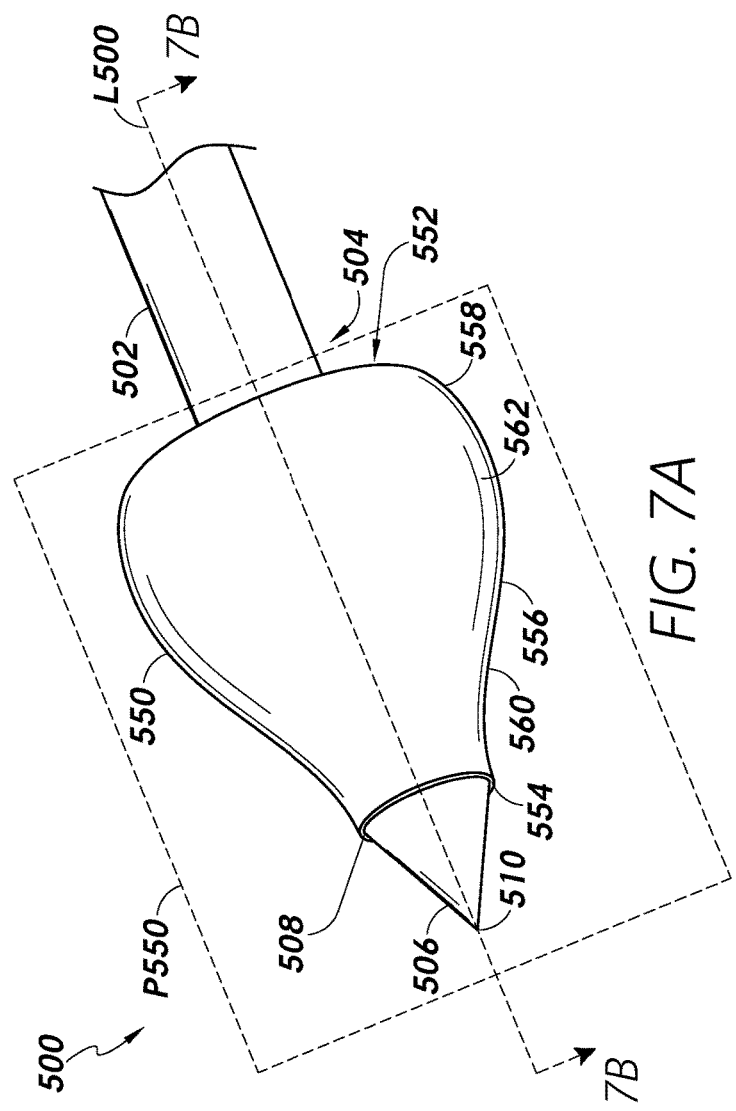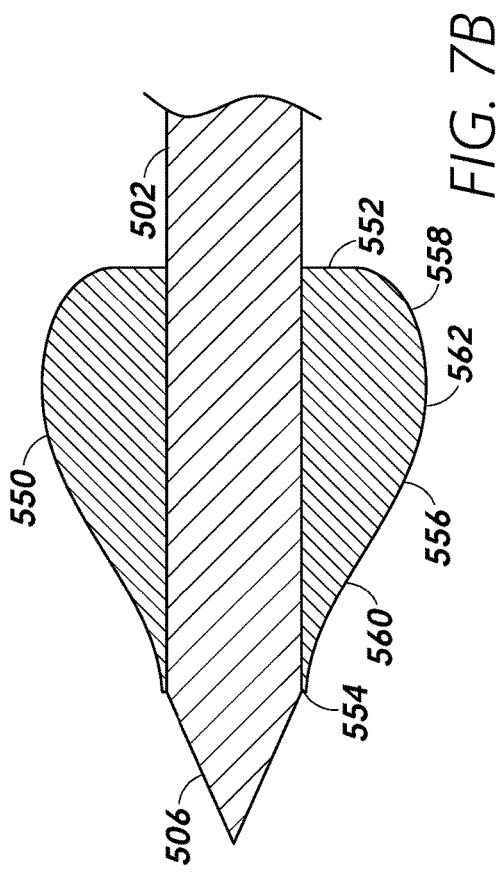

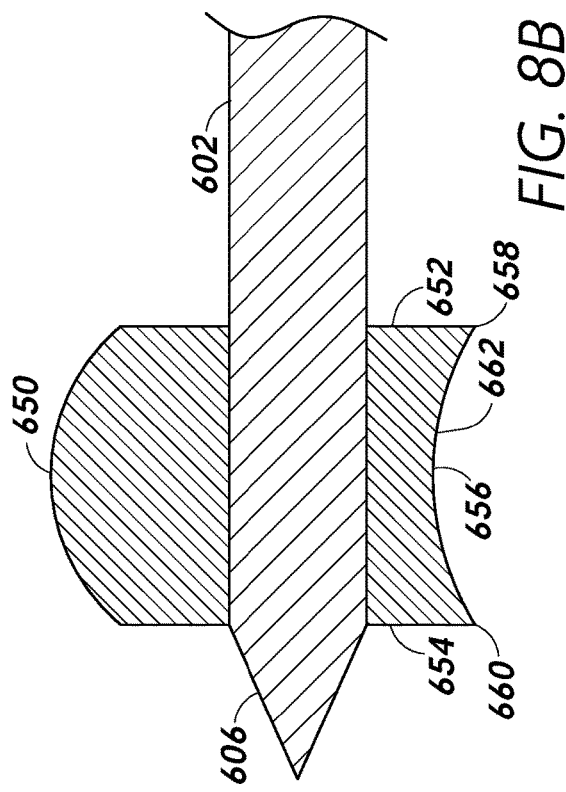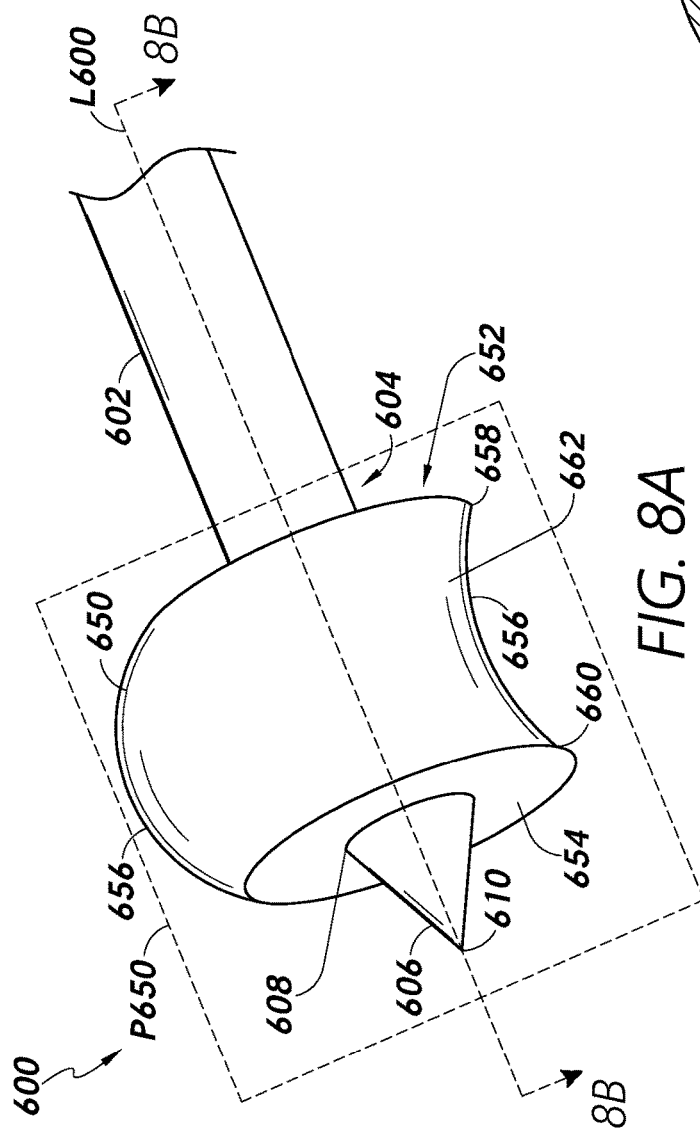

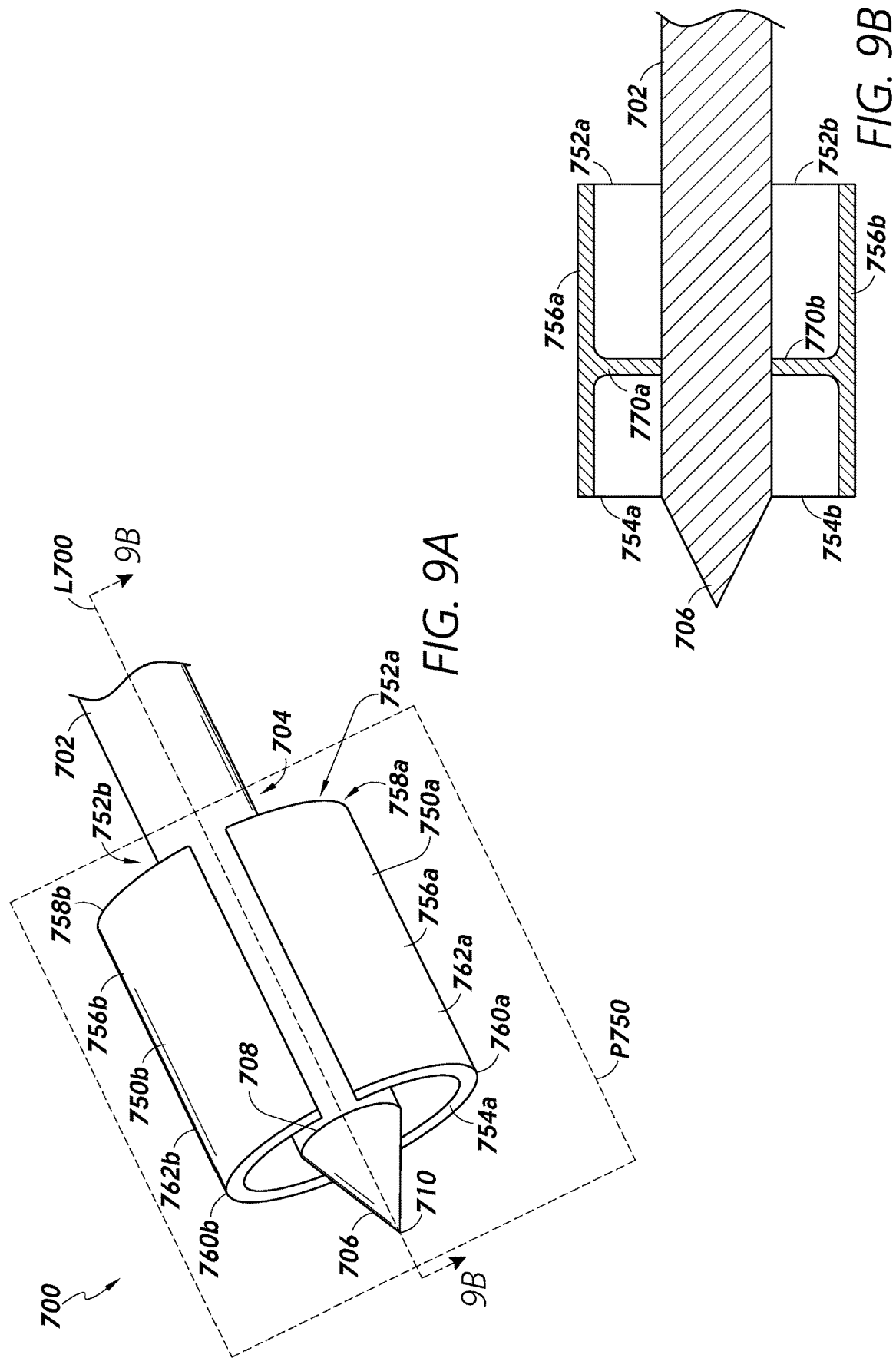

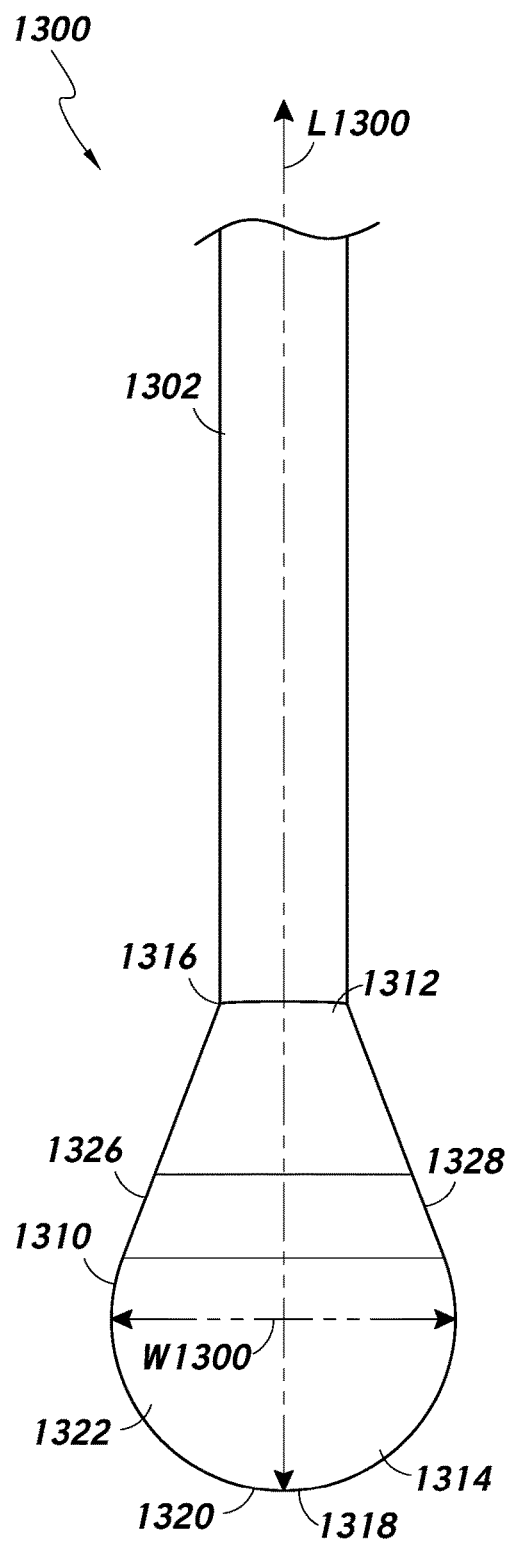
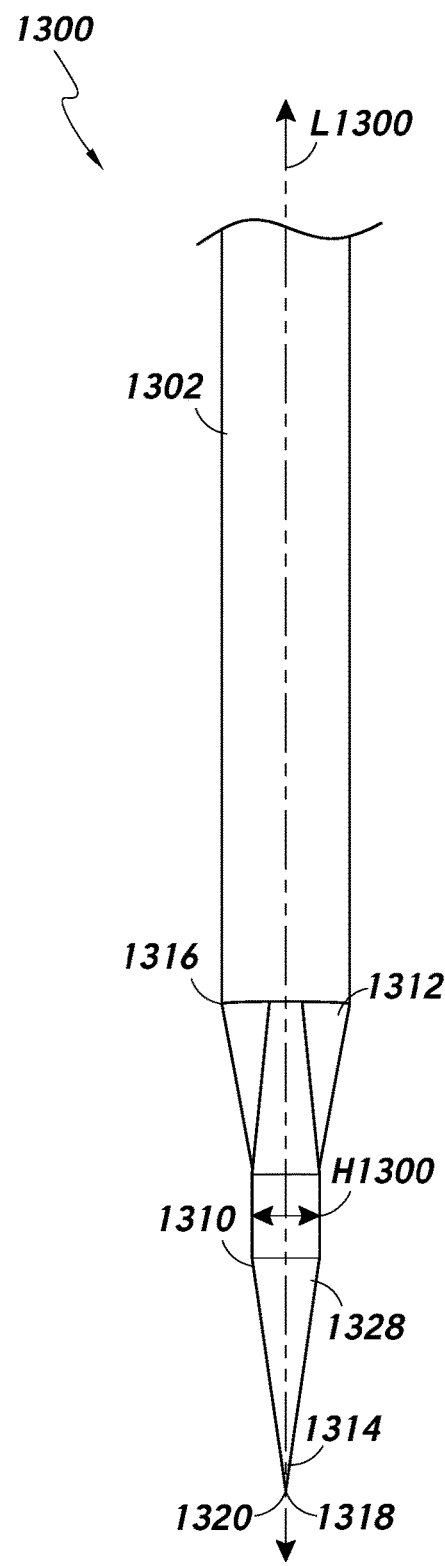
FIG. 14B
FIG. 14C

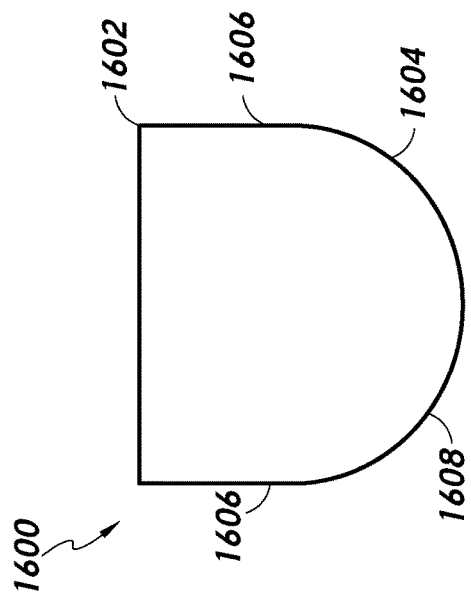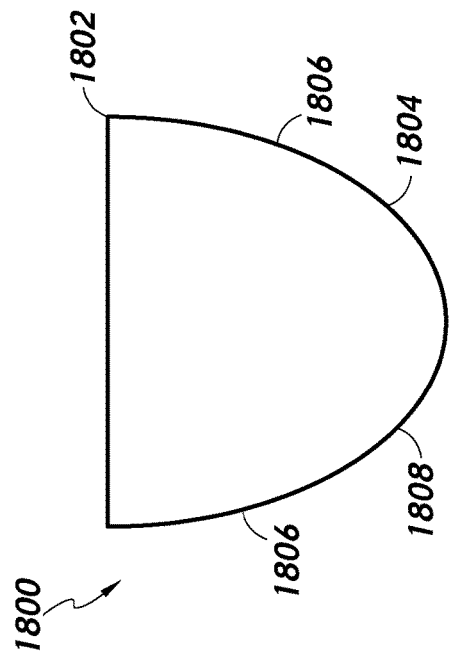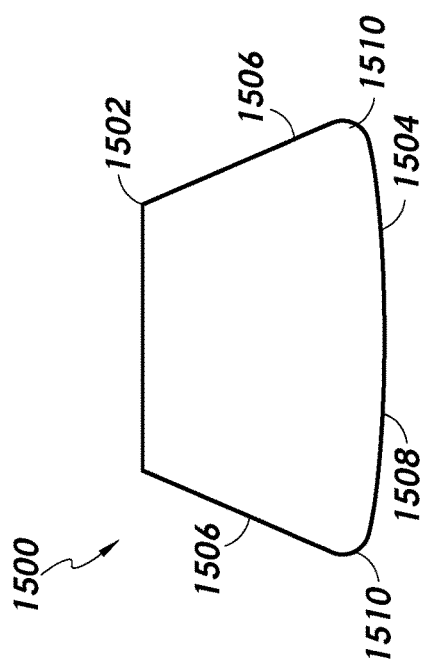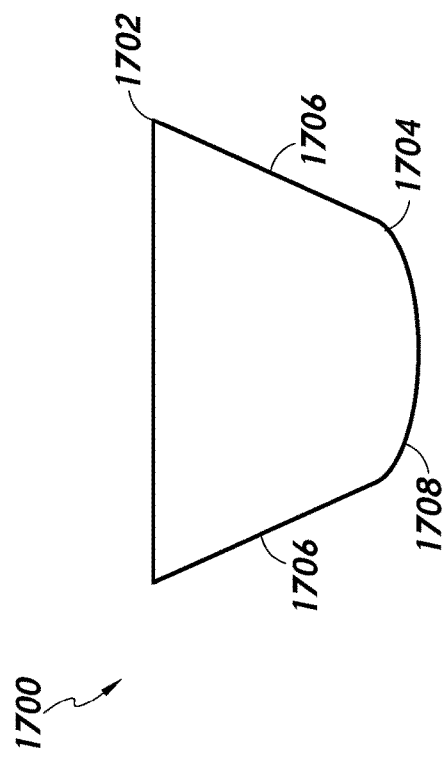

PUNCTURE NEEDLES

CROSS REFERENCE TO RELATED APPLICATIONS

This application is a continuation of PCT International Patent Application Serial No. PCT/US2020/045713, filed Aug. 11, 2020 and entitled PUNCTURE NEEDLES, which claims the benefit of U.S. Provisional Patent Application No. 62/890,528, filed Aug. 22, 2019 and entitled PUNCTURE NEEDLES, the complete disclosures of both of which are hereby expressly incorporated by reference herein in their entireties.

BACKGROUND

Field

The present disclosure generally relates to the field of transcatheter delivery of medical implant devices and/or therapies.

Description of Related Art

Puncture needles can be used in minimally invasive transcatheter approaches to enable delivery of medical implant devices and/or therapies to a target tissue site. Formation of an opening in the tissue of an internal vessel, channel, organ and/or chamber to allow delivery of medical implant devices and/or therapies thereto can require transcatheter delivery of a puncture needle to the target tissue site.

SUMMARY

Described herein are one or more devices, systems and methods relating to puncture needles used in minimally invasive transcatheter approaches, where the puncture needles can be advanced through a delivery catheter lumen without becoming jammed within the lumen, including through one or more bends in the delivery catheter lumen.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

In some implementations, a puncture system can comprise a puncture needle configured to be slidably advanced through a delivery catheter lumen, the puncture needle comprising an elongate portion, and a puncture component associated with a distal end of the elongate portion, the puncture component being configured to puncture tissue. A spacer can be associated with a distal portion of the elongate portion, wherein the spacer can be configured to contact a wall of the delivery catheter lumen to prevent contact between the puncture component and the wall when the puncture component is advanced through a bend in the delivery catheter lumen.

In some embodiments, the spacer comprises a predetermined lateral dimension and a predetermined longitudinal dimension configured to prevent the contact between the puncture component distal end and the wall.

In some embodiments, the spacer comprises a distal end, a proximal end, and a lateral surface between the distal end and the proximal end, wherein the lateral surface is at a predetermined lateral distance from the distal portion of the elongate portion, at least one of the lateral surface and the distal end being configured to contact the wall of the delivery catheter lumen to prevent the contact between the puncture component distal end and the wall.

In some embodiments, the lateral surface comprises a concavely curved surface configured to contact the wall of the delivery catheter lumen. In some embodiments, the lateral surface comprises a convexly curved surface configured to contact the wall of the delivery catheter lumen. In some embodiments, the lateral surface comprises a surface parallel to a longitudinal axis of the puncture needle, the surface being configured to contact the wall of the delivery catheter lumen.

In some embodiments, a longitudinal cross section of the spacer comprises at least one of a segment of a circle, a segment of an oval, and a segment of a teardrop shape, wherein the longitudinal cross section is along a plane extending laterally from the distal portion of the elongate portion along a longitudinal axis of the puncture needle.

In some embodiments, the spacer is symmetrical around an axis collinear with a longitudinal axis of the puncture needle. In some embodiments, the spacer is asymmetrical around an axis collinear with a longitudinal axis of the puncture needle.

In some embodiments, the spacer extends partially circumferentially around the distal portion of the elongate portion. In some embodiments, the spacer is positioned circumferentially around the distal portion of the elongate portion.

In some embodiments, the spacer comprises a ring shape. In some embodiments, a lateral surface of the ring shape comprises a concave curvature. In some embodiments, a lateral surface of the ring shape comprises a convex curvature. In some embodiments, a lateral surface of the ring shape is parallel to an axis collinear with a longitudinal axis of the puncture needle.

In some embodiments, the spacer comprises a plurality of distinct portions positioned around the distal portion of the elongate portion. In some embodiments, the spacer comprises a plurality of lobes positioned circumferentially around the distal portion. In some embodiments, the spacer comprises a plurality of panels extending circumferentially around the distal portion of the elongate portion.

In some embodiments, the spacer is adjacent to the puncture component. In some embodiments, the spacer is a predetermined distance proximal of the puncture component.

In some implementations, a method of puncturing tissue can comprise inserting a puncture needle into a lumen of a delivery catheter, wherein the puncture needle can comprise an elongate portion, a puncture component associated with a distal end of the elongate portion, and a spacer associated with a distal portion of the elongate portion. The method can comprise advancing the puncture component of the puncture needle through a bend in the lumen of the delivery catheter, contacting a wall of the lumen of the delivery catheter with a portion of the spacer associated with the distal portion of the elongate portion to prevent contact between the puncture component and the wall when the puncture component is advanced through the bend in the delivery catheter, extending the puncture component through an outlet opening of the delivery catheter, and puncturing tissue at a target site using the puncture component to form an opening in the tissue.

In some embodiments, the method can comprise enlarging the opening in the tissue, wherein enlarging the opening comprises inserting at least a portion of the spacer into the opening.

In some embodiments, puncturing tissue at the target site comprises puncturing tissue at a left atrial wall location from within a coronary sinus. In some embodiments, the method can comprise inserting the delivery catheter transfemorally into a right atrium and from the right atrium into a coronary sinus through a coronary sinus ostium.

In some implementations, a puncture needle can comprise an elongate portion, and a puncture component associated with a distal end of the elongate portion, the puncture component comprising a blade edge on a distal edge, the blade edge being configured to puncture tissue at a target site, wherein the puncture component is configured to be advanced through a lumen of a delivery catheter without the blade edge sticking to a wall of the lumen at a bend in the delivery catheter.

In some embodiments, the blade edge is on a portion of the distal edge, the distal edge comprising a blunt portion.

In some embodiments, the blade edge comprises a convex curvature. In some embodiments, the blade edge is a convexly-curved blade edge. In some embodiments, the blade edge comprises a segment of a circle. In some embodiments, the blade edge comprises a segment of an oval. In some embodiments, the blade edge comprises a linear blade edge between opposing curved corners.

In some embodiments, a portion of the puncture component proximal of the blade edge has a width wider than a width of the blade edge. In some embodiments, a cross section of a distal portion of the puncture component taken along a plane extending between opposing portions of a pair of lateral surfaces comprises a segment of a circle, the blade edge being on a distal portion of the segment of the circle, and wherein opposing portions of the segment of the circle proximal of the blade edge are blunt.

In some embodiments, a proximal portion of the puncture component has a width narrower than a width of the blade edge. In some embodiments, a proximal portion of the puncture component has a width the same as a width of the blade edge.

In some embodiments, a proximal portion of the puncture component has a height the same as that of a distal portion of the puncture component. In some embodiments, a proximal portion of the puncture component has a height larger than that of a distal portion of the puncture component.

In some implementations, a method of puncturing tissue can comprise inserting a puncture needle through a lumen of a delivery catheter. The puncture needle can comprise an elongate portion and a puncture component associated with a distal end of the elongate portion, and the puncture component can comprise a blade edge on a distal edge of the puncture component. The method can comprise advancing the puncture needle through a bend in the delivery catheter without the puncture component sticking to a wall of the lumen of the delivery catheter, extending the puncture component through an outlet opening on the delivery catheter, and puncturing tissue at a target site using the blade edge to form an opening at the target site.

In some embodiments, the method can comprise enlarging the opening in the tissue, wherein enlarging the opening comprises further inserting the puncture component into the opening.

In some embodiments, a cross section of a distal portion of the puncture component taken along a plane extending between opposing portions of a pair of lateral surfaces comprises a segment of a circle, the blade edge being on a distal portion of the segment of the circle, and wherein opposing portions of the segment proximal of the blade edge are blunt portions, and wherein enlarging the opening comprises inserting the blunt portions into the opening to atraumatically enlarge the opening.

In some embodiments, puncturing tissue at the target site comprises puncturing tissue at a left atrial wall location from within a coronary sinus. In some embodiments, the method can comprise inserting the delivery catheter transfemorally into a right atrium and from the right atrium into a coronary sinus through a coronary sinus ostium.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIGS. 3A and 3B show a perspective view and a longitudinal cross section view of the puncture needle and spacer of FIG. 2, respectively.

FIGS. 4A and 4B show a perspective view and a longitudinal cross section view, respectively, of an example of a puncture needle and an associated spacer which comprises an outwardly curving lateral surface.

FIGS. 5A and 5B show a perspective view and a longitudinal cross section view, respectively, of an example of a puncture needle and an associated spacer which comprises an inwardly curving lateral surface.

FIGS. 6A and 6B show a perspective view and a longitudinal cross section view, respectively, of an example of a puncture needle and an associated spacer comprising an outwardly curving lateral surface, where a distal portion of the lateral surface has a smaller radius of curvature than a proximal portion of the lateral surface.

FIGS. 7A and 7B show a perspective view and a longitudinal cross section view, respectively, of an example of a puncture needle and an associated spacer comprising an outwardly curving lateral surface, where a proximal portion of the lateral surface has a smaller radius of curvature than a distal portion of the lateral surface.

FIGS. 8A and 8B show a perspective view and a longitudinal cross section view, respectively, of an example of a puncture needle and an associated spacer which is asymmetrical around an axis collinear with a longitudinal axis of the puncture needle.

FIGS. 9A and 9B show a perspective view and a longitudinal cross section view, respectively, of an example of a puncture needle and an associated spacer which includes a plurality of panels positioned around an elongate portion of the puncture needle.

FIGS. 14A, 14B and 14C are a perspective view, a top-down plan view, and a side view, of the puncture needle of FIG. 13, respectively.

FIGS. 16, 17, 18 and 19 are top-down plan views of examples of puncture components with a curved blade edge.

DETAILED DESCRIPTION

Figure 1:
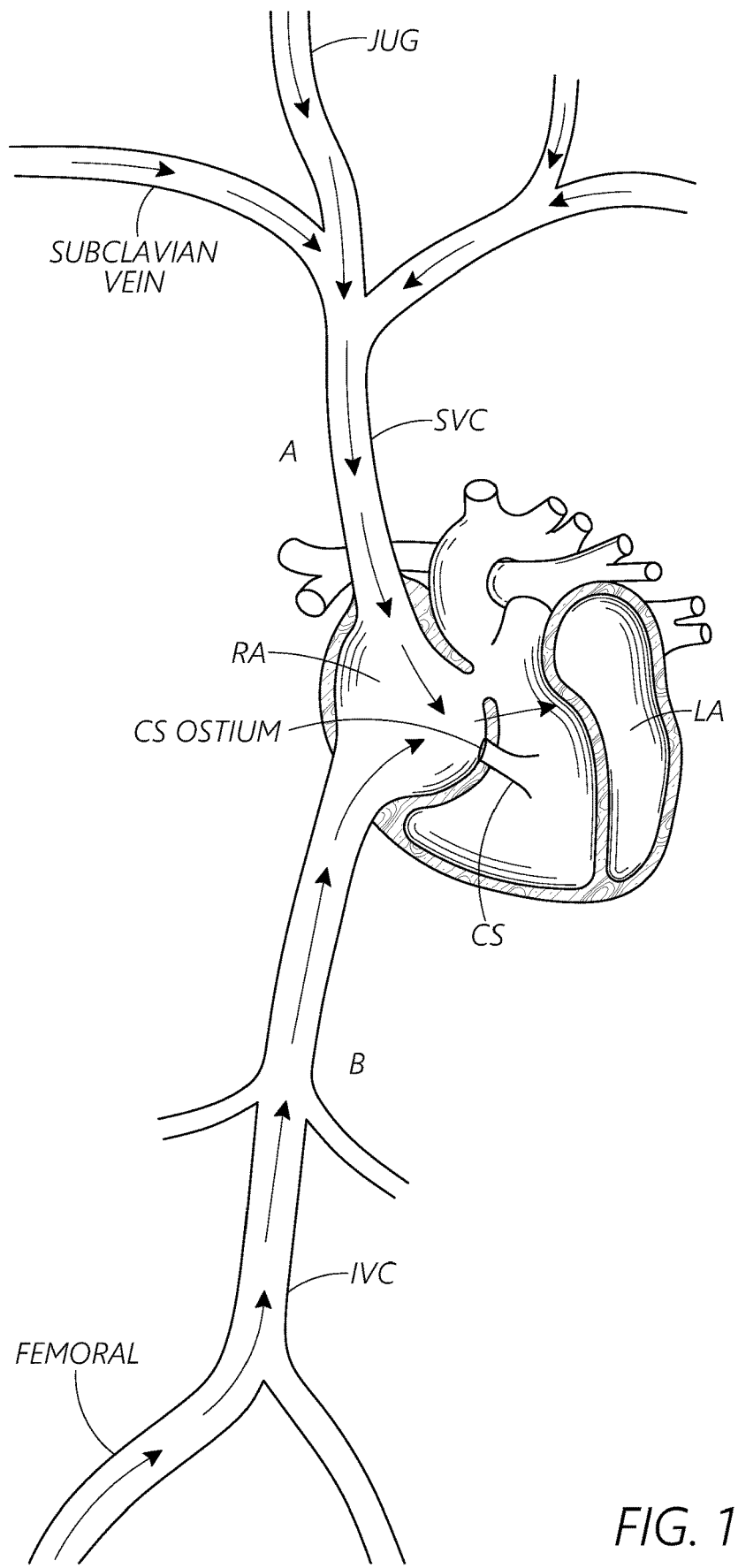
FIG. 1 shows examples of transcatheter pathways to access the heart.

The headings provided herein are for convenience only and do not necessarily affect the scope or meaning of the claimed invention.

The present disclosure relates to systems, devices, and methods relating to minimally invasive transcatheter delivery of medical implant devices and/or therapies to target tissue locations. Described herein are puncture needles which can be advanced from a proximal portion, including a proximal end, to a distal portion, including a puncture needle outlet opening of the distal portion, of a lumen of a delivery catheter positioned within a tortuous anatomical pathway. The puncture needles can be used to pierce tissue at the target tissue locations to enable delivery of the medical implant devices and/or therapies to the target tissue locations. The puncture needles can be advanced through the delivery catheter lumen without becoming jammed within the lumen, including through one or more bends and/or curvatures in the delivery catheter lumen.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Traditional puncture needles used to form openings at target tissue sites in minimally invasive transcatheter approaches can often include a puncture component with a pointed sharp distal end. The target tissue sites can be on a tissue of any number of internal vessels, channels, chambers, and/or organs. Advancing a puncture component with a pointed sharp distal end through a lumen of a delivery catheter positioned in a tortuous anatomical pathway can result in the puncture needle becoming jammed within the delivery catheter lumen. The pointed sharp distal end can contact and become lodged within a wall of the lumen as the puncture component is inserted through the lumen, including through a bend in the delivery catheter lumen. The pointed sharp distal end can prick a portion of the lumen wall, and subsequently become stuck to the lumen wall, thereby preventing insertion of the puncture needle through the delivery catheter to the target tissue site. Traditional puncture needles may not be insertable to a puncture needle outlet opening of a lumen of a delivery catheter already positioned within a tortuous anatomical pathway. For example, traditional puncture needles may not be advanceable from a proximal portion, including a proximal end, to an outlet opening on a distal portion of the delivery catheter lumen without the puncture needles becoming jammed within the delivery catheter lumen. Curves along the anatomical pathway can result in bends in the delivery catheter, and thereby in the delivery catheter lumen, preventing delivery of traditional puncture needles to the target site. A traditional puncture needle may need to be pre-loaded within a delivery catheter lumen such that the puncture needle only needs to be advanced a short distance within a distal portion of the delivery catheter lumen to reach the puncture needle outlet opening positioned at or proximate to a target site. A need to pre-load the puncture needle in the delivery catheter lumen can prevent use of the lumen for other purposes, for example preventing exchange of the puncture needle for other instrumentation, thereby requiring use of a delivery catheter with an increased profile.

Puncture needles described herein can be navigated through a lumen of a delivery catheter positioned in a tortuous anatomical pathway without the puncture needles becoming jammed within the delivery catheter lumen. A puncture needle as described herein can be advanced from a proximal portion, such as a proximal end, to a puncture needle outlet opening on a distal portion of the delivery catheter lumen without the puncture needle becoming stuck within the delivery catheter lumen. The puncture needle can be advanced through one or more bends in the delivery catheter lumen without having any portion of the puncture needle becoming lodged within a delivery catheter lumen wall. The delivery catheter can be first positioned within an anatomical pathway to place the puncture needle outlet opening adjacent or proximate to a target tissue site, and the puncture needle can be subsequently inserted through the already positioned delivery catheter to the puncture needle outlet opening. The delivery catheter does not need to be pre-loaded with the puncture needle prior to positioning the delivery catheter within the anatomical pathway. The puncture needle can be inserted and/or retracted through a delivery catheter already positioned within a patient, enabling exchange of the puncture needle for one or more other instrumentations. Such puncture needles can thereby enable use of delivery catheters with a reduced profile, such as compared to delivery catheters used to accommodate pre-loaded punctured needles.

A puncture needle configured to be advanced through one or more bends of a delivery catheter lumen can include a spacer associated with an elongate portion of the puncture needle, and/or a puncture component which includes a distal edge with a blade edge thereon. The puncture component can be configured to pierce the tissue and can be associated with a distal end of the puncture needle elongate portion. The spacer can be on a distal portion of the elongate portion adjacent to or a predetermined distance proximal of the puncture component. The spacer can comprise at least a portion which extends laterally from the distal portion. The spacer can be configured to contact a wall of the delivery catheter lumen to prevent contact between the puncture component and the wall when the puncture component is advanced through a bend in the delivery catheter lumen. The spacer can be configured to contact the delivery catheter lumen wall so as to provide sufficient distance between a distal end of the puncture component and the lumen wall at and/or proximate to a bend in the lumen such that the distal end cannot contact the lumen wall at and/or proximate to the bend. The spacer can prevent any portion of the puncture component from becoming lodged within the lumen wall, facilitating insertion of the puncture needle through bends in the delivery catheter lumen. A puncture needle comprising a spacer and a puncture component with a pointed sharp distal end can be advanced through one or more bends of a delivery catheter lumen without the puncture needle becoming jammed in the lumen. Avoiding contact between the pointed sharp distal end and the lumen wall can also prevent damage to the lumen wall and/or damage to the pointed sharp distal end to thereby prevent the pointed sharp distal end from becoming unsuitable for piercing tissue to form an opening at the target tissue site.

In some embodiments, the spacer can extend radially from the distal portion the elongate portion. In some embodiments, the spacer can be circumferentially positioned on the distal portion. For example, the spacer can have a ring shape. In some embodiments, the spacer can be partially circumferentially positioned on the distal portion. In some embodiments, the spacer can comprise a plurality of distinct portions arranged around the distal portion. The spacer can comprise a plurality of separate panels. The spacer can comprise a plurality of distinct lateral surface portions. In some embodiments, the spacer can comprise a plurality of distinct portions arranged partially circumferentially around the distal portion.

The spacer may be symmetrical around an axis collinear with a longitudinal axis of the puncture needle. In some embodiments, the spacer is asymmetrical around the axis. A lateral surface of the spacer can be parallel or substantially parallel to a longitudinal axis of the puncture needle, curve and/or bow outwardly, and/or curve and/or bow inwardly. For example, the lateral surface may comprise a convex curvature and/or a concave curvature. In some embodiments, the spacer can comprise a plurality of distinct lateral surface portions which curve and/or bow outwardly. In some embodiments, a shape of the spacer can be predetermined based at least in part on an anticipated direction and/or anticipated degree of curvature of one or more bends in the delivery catheter lumen, including an anticipated direction and/or degree of a sharpest bend. In some embodiments, a shape of a spacer can be selected to facilitate insertion and/or retraction of the spacer through the delivery catheter lumen, for example to reduce friction between the spacer the delivery catheter lumen wall.

In some embodiments, a width and/or a length of the spacer can be selected based on at least a distance between the spacer and a distal end of the puncture component. For example, a spacer at a predetermined distance proximal of the puncture component can comprise a width wider, and/or a length shorter, than that of a spacer adjacent to the puncture component. In some embodiments, at least a portion of the spacer can be inserted into an opening formed at the target tissue site to serve as a dilator to enlarge the opening. The spacer can comprise a width selected based at least in part on a desired enlargement of the opening.

In some embodiments, a puncture needle configured to be advanceable through one or more bends of a delivery catheter lumen can comprise a puncture component with a blade edge on a distal edge. The blade edge can be sharp so as to be able to pierce tissue to form an opening at the target tissue site. In some embodiments, the blade edge can be a curved blade edge, for example a convexly curved blade edge. In some embodiments, the blade edge can comprise a linear portion between opposing curved portions. For example, the blade edge can be a linear portion between rounded corners. The curvature in the blade edge can prevent the blade edge from becoming stuck against the delivery catheter lumen wall. For example, the curved blade edge and/or the blade edge comprising the linear portion between opposing curved corners may contact the delivery catheter lumen wall at a bend in the delivery catheter lumen and glide along the wall without sticking to the wall. A puncture component with a blade edge on a distal edge can comprise a variety of shapes. In some embodiments, the puncture component comprising the blade edge can comprise a rounded paddle shape, the blade edge being on a curved distal edge of the rounded paddle.

Puncture needles described herein can be used to form openings at various target tissue locations within the heart to enable delivery of medical implant devices and/or therapies to the heart. The medical implant devices and/or therapies can be delivered to ameliorate various heart abnormalities. In some embodiments, the puncture needles can be used to form openings on the left atrial wall. For example, delivery of implant devices and/or therapies to the heart can be performed for treatment of elevated pressure in the left atrium. The puncture needles can be used to form openings on portions of the left atrial wall accessible from within the coronary sinus. FIG. 1 shows examples of pathways to the coronary sinus, such that puncture needles can be positioned within the coronary sinus to access the wall of the left atrium (LA). Openings can be formed on the left atrial wall for delivery of any number of medical therapies and/or medical devices, including deployment of expandable shunts into the left atrial wall. As shown in FIG. 1, access into the coronary sinus (CS) can be made through the right atrium (RA) via the coronary sinus ostium (CS ostium). The right atrium can be accessed via the superior vena cava (SVC) or via the inferior vena cava (IVC). For example, a transjugular or trans-subclavian approach can be used to access the right atrium via the superior vena cava. A delivery catheter for delivering a puncture needle can be inserted into the subclavian veins or jugular veins, and advanced into the superior vena cava (e.g., along pathway A). Alternatively, a transfemoral approach can be used to position a delivery catheter into the inferior vena cava (e.g., along pathway B). Other access routes may also be used for insertion of delivery catheters into the vasculature.

Reference herein to "catheters" and/or "delivery catheters" can refer or apply generally to any type of elongate tubular delivery device comprising an inner lumen configured to slidably receive instrumentation, such as for positioning within an atrium or coronary sinus, including for example delivery sheaths and/or cannulas.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

The term "lumen" as used herein can refer to a tubular cavity and/or space, and/or one or more structures which, form, surround and/or define the tubular cavity and/or space, including one or more surfaces which form, surround and/or define the tubular space and/or cavity.

FIGS. 2 through 10 show various examples of puncture needles and associated spacers. In some embodiments, a spacer can be integrally formed with the associated puncture needle, such as with an elongate portion of the puncture needle. In some embodiments, the spacer can be separable from the elongate portion. For example, the spacer can be a distinct and separate component where the spacer is configured to be coupled to the elongate portion. The spacer can be selected for coupling to the elongate portion. Additionally, although the spacer is described as being associated with the elongate portion of the puncture needle, in some embodiments, the spacer can instead be associated with a distal exterior portion of a puncture needle sheath. The puncture needle sheath can be configured to receive the puncture needle and be advanced through a delivery catheter lumen together with the puncture needle to or proximate to a target tissue site. The spacer can be on the distal exterior portion of the puncture needle sheath. In some embodiments, the puncture needle can be advanced relative to the puncture needle sheath such that the puncture needle can be used to pierce the target tissue. In some embodiments, the puncture needle sheath can be retracted relative to the puncture needle after the puncture needle sheath and the puncture needle have been inserted to the target tissue site, so as to facilitate deployment of the puncture needle for piercing the tissue.

The spacers can be implemented in any number of suitable manners. In some embodiments, a spacer can be pre-formed to include one or more configurations as described herein. In some embodiments, a spacer can be configured to transform from a collapsed configuration into a deployed configuration in response to a trigger and/or actuation, the deployed configuration comprising one or more configurations as described herein. In some embodiments, a spacer can comprise an inflatable member, for example, being configured to be inflated prior to or after insertion thereof into an anatomical pathway. The inflatable member can be inflated such that the spacer can assume one or more configurations as described herein.

Although the puncture component as described with reference to FIGS. 2 through 10 have a conical configuration, it will be understood that the puncture component can comprise a number of other configurations, including a pre-curved puncture component with a pointed sharp distal end.

Figure 2:
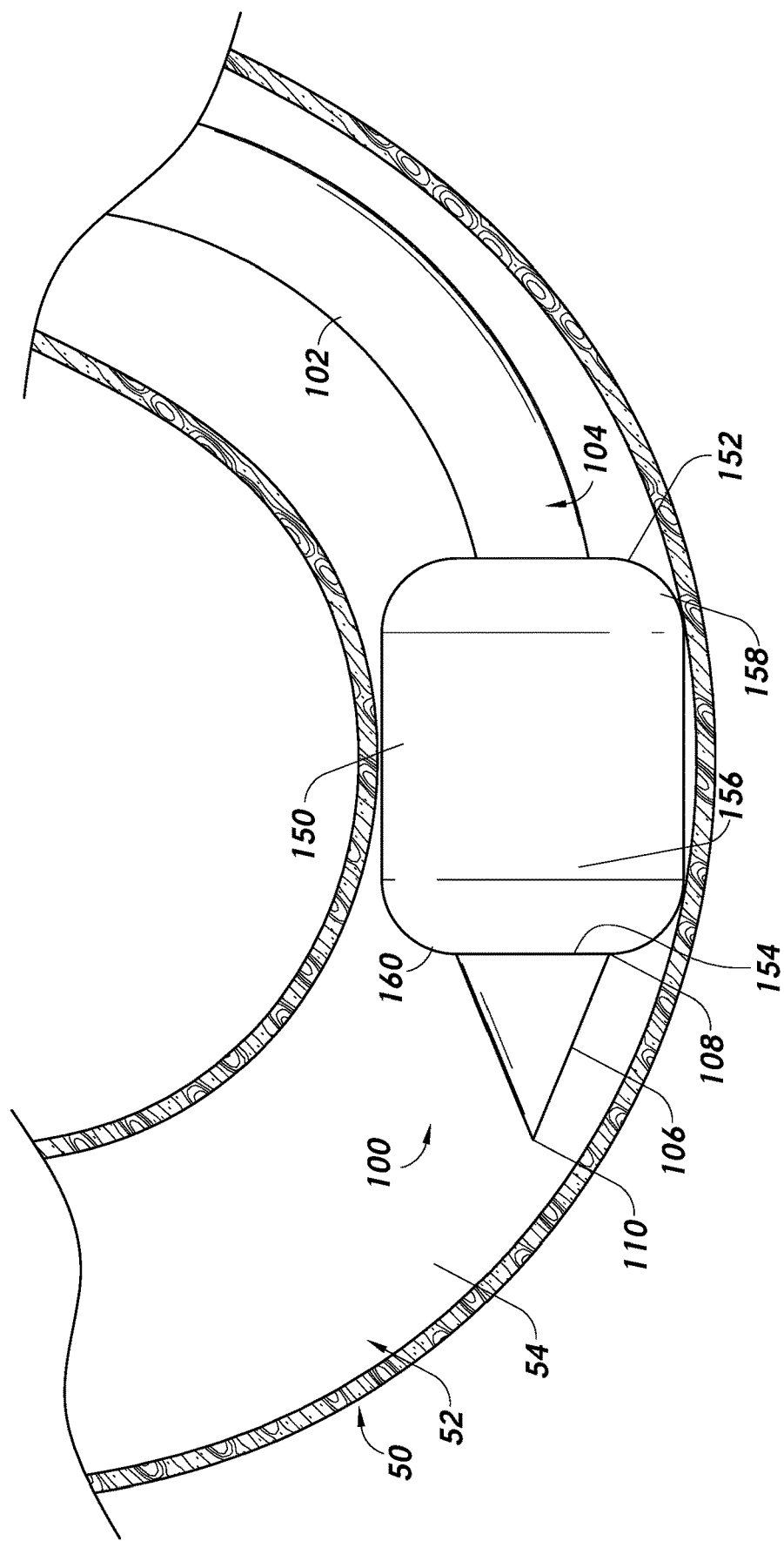
FIG. 2 is a side view of an example of a puncture needle and an associated spacer positioned within a delivery catheter lumen.

FIG. 2 is a side view of an example of a puncture needle 100 and an associated spacer 150 positioned within a lumen 52 of a delivery catheter 50. A cross-sectional view of the delivery catheter 50 is shown. The puncture needle 100 can comprise an elongate portion 102 and the spacer 150 can be on a distal portion 104 of the elongate portion 102. The puncture needle 100 can comprise a puncture component 106 at a distal end (not shown) of the elongate portion 102. The puncture component 106 can comprise a proximal end 108 and a pointed sharp distal end 110. For example, the puncture component 106 can comprise a conical shape.

The spacer 150 can extend radially from the elongate portion and can be configured to contact a wall 54 of the lumen 52 while the puncture needle 100 is advanced through the lumen 52 to prevent contact between the wall 54 of the lumen 52 and the pointed sharp distal end 110 of the puncture component 106. Contact between the pointed sharp distal end 110 and the wall 54 can result in the pointed sharp distal end 110 becoming lodged within the wall 54 and/or stuck to the wall 54, causing the puncture needle 100 to become jammed within the lumen 52. Contact between the pointed sharp distal end 110 and the wall 54 can damage the delivery catheter 50 and/or the pointed sharp distal end 110. The spacer 150 can contact the wall 54 such that sufficient distance is maintained between the pointed sharp distal end 110 and the wall 54 while the puncture needle 100 is advanced through the delivery catheter lumen 52, including while the puncture needle 100 is advanced through a bend in the lumen 52, to prevent contact between the pointed sharp distal end 110 and the wall 54. The puncture needle 100 can thereby be inserted and/or retracted through the delivery catheter lumen 52 without being jammed within the lumen 52, allowing the puncture needle 100 to be exchangeable with one or more other surgical instruments, including instrumentations for delivering one or more therapies and/or one or more medical devices to a target tissue site.

The spacer 150 can have a proximal end 152 and a distal end 154, and a lateral portion 156 extending between the proximal end 152 and the distal end 154. The spacer 150 can have a proximal edge portion 158, such as an edge along which the proximal end 152 meets the lateral portion 156, and a distal edge portion 160, such as an edge along which the distal end 154 meets the lateral portion 156. In the example shown in FIG. 2, the puncture needle 100 is positioned in a bend of the delivery catheter lumen 52. In some embodiments, to prevent contact between the pointed sharp distal end 110 and the wall 54, the lateral portion 156 of the spacer 150 can contact the wall 54 of the delivery catheter lumen 52 along an inner edge of the radius of curvature. In some embodiments, the proximal end 152 and/or the proximal edge portion 158, and the distal end 154 and/or the distal edge portion 160, can contact the wall 54 along on an outer edge of the radius of curvature of the bend. Contact between the wall 54 and the lateral portion 156, the proximal end 152, the proximal edge portion 158, the distal end 154, and/or the distal edge portion 160 can provide sufficient space between the pointed sharp distal end 110 and the wall 54 such that the pointed sharp distal end 110 does not prick the wall 54 while the puncture needle 100 is advanced through the bend.

In some embodiments, the spacer 150 can be adjacent to the puncture component 106. For example, the proximal end 108 of the puncture component 106 can be adjacent to the distal end 154 of the spacer 150. In some embodiments, the distal end 154 of the spacer 150 can be adjacent to the distal end of the elongate portion 102. The distal end 154 of the spacer 150 can be adjacent to the proximal end 108 of the puncture component 106. Alternatively, the spacer 150 can be at a predetermined distance proximal of the puncture component 106. For example, the distal end 154 of the spacer 150 can be a predetermined distance proximal of the proximal end 108 of the puncture component 106. In some embodiments, the distal end 154 of the spacer 150 can be at a predetermined distance proximal of the distal end of the elongate portion 102.

FIG. 3A is a perspective view of the puncture needle 100 and the spacer 150. The spacer 150 can be circumferentially positioned around the distal portion 104 of the elongate portion 102. For example, the spacer 150 can have a ring shape. In some embodiments, the spacer 150 can be coaxial with a longitudinal axis $L_{100}$ of the puncture needle 100. The spacer 150 can be symmetrical around an axis which is collinear with a longitudinal axis $L_{100}$ of the puncture needle 100. The longitudinal axis $L_{100}$ can extend centrally along a length of the elongate portion 102, such as through a proximal portion (not shown) and the distal portion 104 of the elongate portion 102.

FIG. 3B shows a longitudinal cross-sectional view of the spacer 150. The longitudinal cross section can be taken along a longitudinal cross-sectional plane $P_{150}$. The longitudinal cross-sectional plane $P_{150}$ can extend laterally from the distal portion 104 along the longitudinal axis $L_{100}$ of the puncture needle 100. For example, a longitudinal cross section of the spacer 150 can comprise a rectangular or substantially rectangular shape. The lateral portion 156 can comprise a lateral surface 162 parallel or substantially parallel to the longitudinal axis $L_{100}$ of the puncture needle 100.

A width and/or a length of the spacer 150 can be predetermined to prevent contact between the pointed sharp distal end 110 and the delivery catheter lumen wall 54. The length can be a longitudinal dimension parallel or substantially parallel to the longitudinal axis $L_{100}$. For example, the length can be a dimension extending between the proximal end 152 and the distal end 154 of the spacer 150. The width can be a lateral dimension which is perpendicularly or substantially perpendicularly to the length, such as perpendicular or substantially perpendicular to the longitudinal axis $L_{100}$ of the puncture needle 100. For example, the width can extend between opposing portions of the lateral surface 162.

As described herein, the spacer 150 can be adjacent to, or alternatively, a predetermined distance proximal of, the puncture component 106. In some embodiments, the width and/or the length of the spacer 150 can be predetermined based at least in part on a distance between the spacer 150 and the pointed sharp distal end 110 of the puncture component 106. In some embodiments, the width can be directly related to the distance between the spacer 150, such as the distal end 154, and the pointed sharp distal end 110. For example, a wider width can be selected for a spacer positioned at a distance proximal of the puncture component 106 than for a spacer positioned adjacent to the puncture component 106. In some embodiments, the length of the spacer 150 can be inversely related to a distance between the spacer 150, such as the distal end 154, and the pointed sharp distal end 110. For example, a shorter length can be selected for a spacer positioned at a distance proximal of the puncture component 106 than for a spacer positioned adjacent to the puncture component 106. In some embodiments, the length does not depend on the distance between the spacer 150 and the pointed sharp distal end 110.

In some embodiments, the proximal end 152 and/or the distal end 154 can be a planar or substantially planar surface. Alternatively, the spacer 150 can comprise a proximal taper and/or a distal taper, such as a taper from the lateral portion 156 toward the proximal end 152 and/or the distal end 154, respectively. The taper may include a curved and/or linear taper. In some embodiments, the spacer 150 can comprise a proximal taper and/or a distal taper to facilitate retraction and/or insertion of the spacer 150 through the delivery catheter lumen 52.

In some embodiments, the spacer 150 can serve as a dilator configured to be inserted into the opening formed at a target tissue site by the puncture component 106 so as to enlarge the opening. The puncture needle 100 can be advanced further after the opening is formed such that at least a portion of the spacer 150 is inserted into the opening. In some embodiments, the width of the spacer 150 can be selected based at least in part on a desired dilation of the opening. In some embodiments, the width of the spacer 150 can be selected so as not to be too large to impede insertion of the spacer 150 into the opening. In some embodiments, the spacer 150 can comprise a distal taper to facilitate insertion of the spacer 150 into the opening. In some embodiments, the spacer 150 is not configured to be inserted into the opening. In some embodiments, the distal end 154 of the spacer 150 can be planar or substantially planar to prevent or reduce insertion of the spacer 150 into the opening.

FIGS. 4 through 10 show additional examples of spacers. FIG. 4A is a perspective view of an example of a puncture needle 200 and an associated spacer 250 comprising an outward-curving lateral surface 262. FIG. 4B shows a longitudinal cross-sectional view of the spacer 250. Referring to FIG. 4A, the spacer 250 can be circumferentially positioned around an elongate portion 202 of the puncture needle 200. For example, the spacer 250 can extend radially from a distal portion 204 of the elongate portion 202. The spacer 250 can have a ring shape. In some embodiments, the spacer 250 can be coaxial with the puncture needle 200. The spacer 250 can be symmetrical around an axis collinear with the longitudinal axis $L_{200}$ of the puncture needle 200. The spacer 250 can have a proximal end 252 and a distal end 254, and a lateral portion 256 between the proximal end 252 and the distal end 254. The lateral portion 256 can comprise a lateral surface 262 which comprises a convex curvature. For example, the lateral surface 262 can curve and/or bow outward. Opposing portions of the lateral portion 256, such as opposing portions of the lateral surface 262, can contact a delivery catheter lumen wall along an inner edge and an outer edge of a curvature in the delivery catheter lumen.

Referring to FIG. 4B, a longitudinal cross section of the spacer 250 along the longitudinal cross-sectional plane $P_{250}$ can comprise a segment of a circle. For example, the convex curvature can have a uniform or substantially uniform radius of curvature. In some embodiments, the longitudinal cross section along the longitudinal cross-sectional plane $P_{250}$ can comprise a segment of an oval. The longitudinal cross-sectional plane $P_{250}$ can extend laterally from the distal portion 204 of the elongate portion 202 along the longitudinal axis $L_{200}$. The lateral portion 256 comprising the outward curvature can reduce contact, thereby reducing friction, between the spacer 250 and a delivery catheter lumen wall to facilitate insertion and/or retraction of the puncture needle 200 through the delivery catheter lumen.

FIG. 5A is a perspective view of an example of a puncture needle 300 and an associated spacer 350 comprising an inward curving lateral surface 362. FIG. 5B shows a longitudinal cross-sectional view of the spacer 350. Referring to FIG. 5A, the spacer 350 can be circumferentially positioned around an elongate portion 302 of the puncture needle 300, such as around a distal portion 304 of the elongate portion 302. The spacer 350 can have a ring shape. In some embodiments, the spacer 350 can be coaxial with the puncture needle 300. The spacer 350 can be symmetrical around an axis which is collinear with a longitudinal axis $L_{300}$ of the puncture needle 300. The spacer 350 can have a proximal end 352, a distal end 354, and a lateral portion 356 between the proximal end 352 and the distal end 354. The lateral portion 356 can have a lateral surface 362. The lateral surface 362 can comprise a concave curvature. For example, the lateral surface 362 can curve or bow inward.

Referring to FIG. 5B, a longitudinal cross-sectional view of the spacer 350 is shown. The longitudinal cross section of the spacer 350 can be taken along the longitudinal cross-sectional plane $P_{350}$. The longitudinal cross-sectional plane $P_{350}$ can extend laterally from the distal portion 304 of the elongate portion 302 along the longitudinal axis $L_{300}$. The longitudinal cross section of the lateral portion 356 can comprise a concave curvature, the lateral surface 362 curving inward. In some embodiments, the concave curvature can have a uniform radius of curvature. For example, the concave curvature can comprise a segment of a circle. In some embodiments, the radius of curvature of the concave curvature can be non-uniform. For example, the concave curvature can comprise a segment of an oval.

The spacer 350 can have a proximal edge portion 358, such as an edge along which the proximal end 352 meets the lateral portion 356, and a distal edge portion 360, such as an edge along which the distal end 354 meets the lateral portion 356. In some embodiments, when the puncture needle 300 is advanced through a bend in a delivery catheter lumen, the lateral portion 356 can contact a wall of the delivery catheter lumen along an inner edge of the curvature in the bend. In some embodiments, the proximal end 352 and/or the proximal edge portion 358, and the distal end 354 and/or the distal edge portion 360, can contact the wall along on an outer edge of the curvature in the delivery catheter lumen. In some embodiments, the concave curvature of the lateral portion 356 can provide reduced contact between the spacer 350 and the delivery catheter lumen wall, thereby reducing friction between the spacer 350 and the delivery catheter lumen wall so as to facilitate insertion and/or retraction of the puncture needle 300.

FIG. 6A is a perspective view of an example of a puncture needle 400 and an associated spacer 450, where the spacer 450 includes an outwardly curving lateral surface 462, a distal portion of the lateral surface 462 having a smaller radius of curvature than a proximal portion of the lateral surface 462. FIG. 6B shows a longitudinal cross-sectional view of the spacer 450. Referring to FIG. 6A, the spacer 450 can be circumferentially positioned around an elongate portion 402 of the puncture needle 400, such as a distal portion 404 of the elongate portion 402. In some embodiments, the spacer 450 can be coaxial with the puncture needle 400. The spacer 450 can be symmetrical around an axis collinear with a longitudinal axis $L_{400}$ of the puncture needle 400. The spacer 450 can have a proximal end 452, a distal end 454, and a lateral portion 456 between the proximal end 452 and the distal end 454. The lateral portion 456 can have a lateral surface 462. The lateral portion 456 can comprise an outward bow and/or curvature with a non-uniform radius of curvature. For example, the lateral surface 462 can comprise a convex curvature with a non-uniform radius of curvature, where the radius of curvature increases along a direction extending from the distal end 454 to the proximal end 452. A distal portion 460 of the lateral surface 462 can have a smaller radius of curvature than a proximal portion 458 of the lateral surface 462.

Referring to FIG. 6B, a longitudinal cross section of the spacer 450 taken along the longitudinal cross-sectional plane $P_{450}$ is shown. The longitudinal cross-sectional plane $P_{450}$ can extend laterally from the distal portion 404 along the longitudinal axis $L_{400}$. As shown in the longitudinal cross section of the spacer 450, the lateral surface 462 can comprise a convex curvature, where the radius of curvature increases along a direction extending from the distal end 454 toward the proximal end 452. A width of the spacer 450 can generally decrease along a direction extending from the distal end 454 to the proximal end 452. The width of the spacer 450 can be a dimension which extends between opposing portions of the lateral surface 462. In some embodiments, the longitudinal cross section of the spacer 450 can comprise a segment of a teardrop shape, where a wider portion of the segment is oriented toward the puncture component 406 of the puncture needle 400. When the puncture needle 400 is inserted through a bend in a delivery catheter lumen, opposing portions of the lateral surface 462 can contact a wall of the delivery catheter lumen along an inner edge and an outer edge of the bend. For example, opposing portions of the distal portion 460 of the lateral surface 462 can contact the delivery catheter lumen wall along the inner edge and outer edge of the bend.

FIG. 7A is a perspective view of an example of a puncture needle 500 and an associated spacer 550, where the spacer 550 includes an outwardly curving lateral surface 562, a proximal portion 558 of the lateral surface 562 having a smaller radius of curvature than a distal portion 560 of the lateral surface 562. FIG. 7B shows a longitudinal cross-sectional view of the spacer 550. The spacer 550 can have an orientation opposite that of the spacer 450 described with reference to FIGS. 6A and 6B. The spacer 550 can comprise other features which are the same as or similar to that of the spacer 450. For example, referring to FIG. 7A, the spacer 550 can be circumferentially positioned around a distal portion 504 of the elongate portion 502. In some embodiments, the spacer 550 can be coaxial with the puncture needle 500. The spacer 550 can have symmetry around an axis collinear with a longitudinal axis $L_{500}$ of the puncture needle 500. Referring to FIG. 7B, a longitudinal cross section of the spacer 550 taken along the longitudinal cross-sectional plane $P_{550}$ shows that the lateral surface 562 of a lateral portion 556 extending between a proximal end 552 and a distal end 554 can have a convex curvature. The convex curvature can have a radius of curvature which decreases along a direction extending from the distal end 554 toward the proximal end 552. The longitudinal cross-sectional plane $P_{550}$ can extend laterally from the distal portion 504 along the longitudinal axis $L_{500}$. A width of the spacer 550, such as a dimension which extends between opposing portions of the lateral surface 562, can generally increase along a direction extending from the distal end 554 to the proximal end 552. In some embodiments, the longitudinal cross section of the spacer 550 can comprise a segment of a teardrop shape, where a wider portion of the segment is oriented away from the puncture component 506 of the puncture needle 500. When the puncture needle 500 is inserted through a bend in a delivery catheter lumen, opposing portions of the lateral surface 562 can contact a wall of the delivery catheter lumen along an inner edge and an outer edge of the bend. For example, opposing portions of the proximal portion 558 of the lateral surface 562 can contact the delivery catheter lumen wall along the inner edge and outer edge of the bend.

FIG. 8A is a perspective view of an example of a puncture needle 600 and an associated spacer 650 which is asymmetrical around an axis collinear with a longitudinal axis $L_{600}$ of the puncture needle 600. The puncture needle 600 can have a puncture component 606 at a distal end of an elongate portion. The spacer 650 can be coaxial with the puncture needle 600. FIG. 8B is a longitudinal cross-sectional view of the puncture needle 600. Referring to FIG. 8A, the spacer 650 can be circumferentially positioned around a distal portion 604 of the elongate portion 602. The spacer 650 can have a proximal end 652, a distal end 654, and a lateral portion 656 between the proximal end 652 and the distal end 654. The lateral portion 656 can have a lateral surface 662. The lateral surface 662 and the proximal end 652 and distal end 654 can meet to form a proximal edge portion 658 and a distal edge portion 660, respectively. The lateral portion 656 can comprise both an outward curvature and an inward curvature. For example, opposing portions of the lateral surface 662 can comprise a convex curvature and a concave curvature such that the spacer 650 is asymmetrical around the longitudinal axis $L_{600}$.

Referring to FIG. 8B, a longitudinal cross-sectional view of the spacer 650 is shown. A longitudinal cross section of the spacer 650 along the longitudinal cross-sectional plane $P_{650}$ is shown. The longitudinal cross-sectional plane $P_{650}$ can extend laterally from the distal portion 604 in opposite directions along the longitudinal axis $L_{600}$. The longitudinal cross section of the spacer 650 taken along the cross-sectional plane $P_{650}$ shows that the lateral surface 662 can comprise both a convex curvature and a concave curvature. For example, a first portion of the lateral surface 662 can comprise the convex curvature and a portion of the lateral surface 662 opposite the first portion can comprise the concave curvature. In some embodiments, the radius of curvature of the convex curve and/or the concave curve can be uniform or substantially uniform. In some embodiments, the radius of curvature of the convex curve and/or the concave curve can be non-uniform.

In some embodiments, the orientation of the convex curvature and the concave curvature can depend on an anticipated curvature of a known bend in the anatomical pathway into which a delivery catheter is advanced. For example, the orientation can be selected based on a direction of an anticipated sharpest bend in the anatomical pathway, and thereby based on a direction of an anticipated sharpest bend in the delivery catheter lumen. In some embodiments, the concave portion of the lateral surface 662 can be configured to be oriented toward an outer edge of the bend and the convex portion of the lateral surface 662 can be oriented toward an inner edge of the bend. In some embodiments, the convex portion of the lateral surface 662 can contact a delivery catheter lumen wall along the inner edge of the bend. In some embodiments, the proximal end 652 and/or the proximal edge portion 658, and the distal end 654 and/or the distal edge portion 660, can contact the delivery catheter lumen wall along the outer edge.

In some embodiments, a spacer asymmetrical around an axis collinear with a longitudinal axis of the puncture needle can comprise another configuration. For example, opposing lateral surface portions can comprise a curved portion, such as a convex and/or concave curvature, and a portion parallel or substantially parallel to the longitudinal axis.

FIGS. 9A and 9B show an example of a puncture needle 700 and an associated spacer 750 which includes a pair of panels positioned in an opposing manner on an elongate portion 702 of the puncture needle 700. The puncture needle 700 can have a puncture component 706 at a distal end of the elongate portion 702. FIG. 9A is a perspective view, while FIG. 9B is a longitudinal cross-sectional view. The spacer 750 can include a plurality of discrete panels arranged around a distal portion 704 of the elongate portion 702. For example, the spacer 750 can include a first panel 750a and a second panel 750b arranged around the distal portion 704 of the elongate portion 702. The first panel 750a and the second panel 750b can be arranged in opposing fashion around the distal portion 704. The panels 750a, 750b can be partially circumferentially arranged around the distal portion 704. For example, the panels 750a, 750b can each comprise an arcuate shape and can be spaced from one another by a pair of opposing gaps (only one of the gaps is visible in FIG. 9A). The panels 750a, 750b can be arranged to surround a corresponding portion of the elongate portion 702. In some embodiments, the first panel 750a and the second panel 750b can have the same or similar configurations. In some embodiments, the separation between the panels can provide improved flexibility to facilitate insertion of the spacer 750 through a delivery catheter lumen placed within tortuous anatomical pathways. The gaps separating the first panel 750a and the second panel 750b can be predetermined to provide improved flexibility while allowing the spacer 750 to maintain a desired distance between the puncture component 706 and the delivery catheter lumen wall.

The first panel 750a and the second panel 750b can each comprise a respective proximal end 752a, 752b, a respective distal end 754a, 754b, and a respective lateral portion 756a, 756b. Each lateral portion 756a, 756b can comprise a respective lateral surface 762a, 762b. The first panel 750a can comprise a proximal edge portion 758a, such as an edge along which the proximal end 752a meets the lateral portion 756a, and a distal edge portion 760a, such as an edge along which the distal end 754a meets the lateral portion 756a. The second panel 750b can comprise a second proximal edge portion 758b, such as an edge along which the second proximal end 752b meets the second lateral portion 756b, and a second distal edge portion 760b, such as an edge along which the second distal end 754b meets the second lateral portion 756b. For example, as the puncture needle 700 is advanced through a bend in a delivery catheter lumen, the first lateral surface 762a can contact a lumen wall along an inner edge of the bend. In some embodiments, the second proximal end 752b and/or the second proximal edge portion 758b, and the second distal end 754b and/or the second distal edge portion 760b, can contact the lumen wall along an outer edge of the bend. In some embodiments, the second lateral surface 762b can contact a lumen wall along an inner edge of the bend, and the first proximal end 752a and/or the first proximal edge portion 758a, and the first distal end 754a and/or the first distal edge portion 760a, can contact the lumen wall along an outer edge of the bend.

The cross-sectional view of FIG. 9B is taken along the longitudinal cross-sectional plane $P_{750}$. The longitudinal cross-sectional plane $P_{750}$ can extend laterally from the distal portion 704 of the elongate portion 702 along the longitudinal axis $L_{700}$. The longitudinal cross section of the first panel 750a and the second panel 750b are shown. In some embodiments, a connector member 770a, 770b can couple the first panel 750a and the second panel 750b to the distal portion 704 of the elongate portion 702. The lateral portions 756a, 756b, of the first panel 750a and the second panel 750b can be parallel or substantially parallel to the elongate portion 702.

It will be understood that the number and/or shape of the panels 750a, 750b are used for illustrative purposes. In some embodiments, a spacer can have more than two panels arranged around an elongate portion of a puncture needle. In some embodiments, one or more of the panels can comprise a different shape. For example, one or more of the panels can comprise one or more shapes as described herein, including a panel comprising an outward curvature and/or an inward curvature. A lateral surface of the panel can comprise a convex curvature and/or a concave curvature, where the curvature may or may not have a uniform radius of curvature.

Figure 10C:
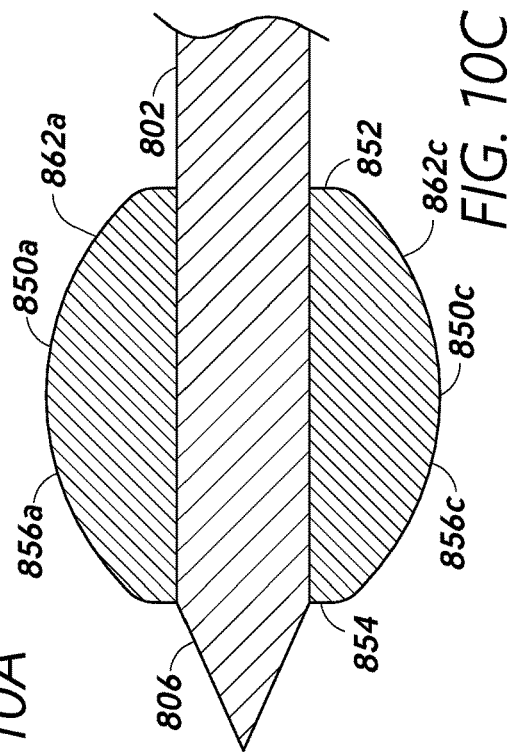
FIGS. 10A, 10B, and 10C show a perspective view, a view from a distal end, and a longitudinal cross section view, respectively, of an example of a puncture needle and an associated spacer which includes a plurality of distinct outwardly curving portions circumferentially positioned around an elongate portion.
Figure 10A:
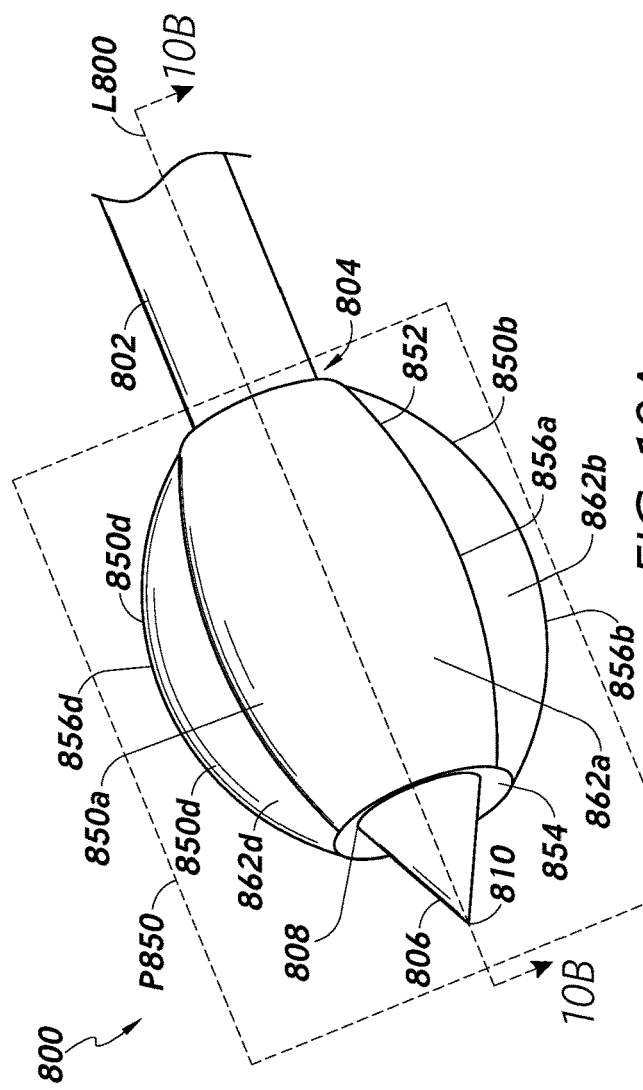
Figure 10B:
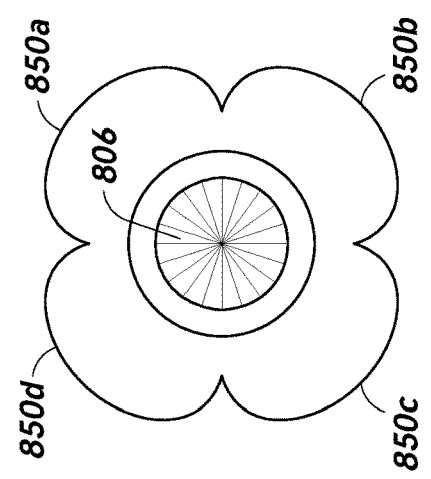

FIGS. 10A, 10B and 10C show an example of a puncture needle 800 and an associated spacer 850 comprising a plurality of distinct outwardly curving portions circumferentially positioned around an elongate portion 802 of the puncture needle 800. The puncture needle 800 can have a puncture component 806 at a distal end of the elongate portion 802. FIG. 10A is a perspective view of the puncture needle 800 and FIG. 10B is a view of the puncture needle 800 from a distal end. Referring to FIG. 10A, the spacer 850 can comprise four portions 850a, 850b, 850c (not shown), 850d positioned around a distal portion 804 of the elongate portion 802. In some embodiments, the four portions 850a, 850b, 850c, 850d can be four uniform or substantially uniform portions evenly distributed around the distal portion 804, each of the four portions 850a, 850b, 850c, 850d comprising an outward bow. The four portions 850a, 850b, 850c, 850d can be four distinct, and uniform or substantially uniform, lobes evenly distributed around the circumference of the distal portion 804. The four portions 850a, 850b, 850c, 850d are shown in FIG. 10B.

The spacer 850 can have a proximal end 852 and a distal end 854. Each of the four portions 850a, 850b, 850c, 850d can have a corresponding lateral portion 856a, 856b, 856c, 856d between the proximal end 852 and the distal end 854. Each lateral portion 856a, 856b, 856c, 856d can comprise a corresponding lateral surface 862a, 862b, 862c, 862d. In some embodiments, each of the lateral portions 856a, 856b, 856c, 856d can comprise an outward curvature, such as a convex curvature. For example, each of the four distinct lateral surfaces 862a, 862b, 862c, 862d can comprise a convex curvature. The lateral portions 856a, 856b, 856c, 856d can each comprise a convex curvature along both a longitudinal axis and a lateral axis, where the lateral axis is perpendicular or substantially perpendicular to the longitudinal axis. As described in further detail herein, the longitudinal axis can extend along a direction parallel or substantially parallel with a longitudinal axis of the puncture needle 800, $L_{800}$. For example, the longitudinal axis can be collinear with $L_{800}$. In some embodiments, a lateral cross section of each lateral portion 856a, 856b, 856c, 856d along a plane extending along the lateral axis can comprise a convex curvature. The radius of curvature of the convex curve may or may not be uniform. In some embodiments, the lateral cross section can comprise a segment of a circle. In some embodiments, the lateral cross section can comprise a segment of an oval.

In FIG. 10C, a longitudinal cross-sectional view of the spacer 850 is shown. Specifically, a longitudinal cross-sectional view of the spacer 850 along the longitudinal cross-sectional plane $P_{850}$ is shown. The longitudinal cross-sectional plane $P_{850}$ can extend laterally from the distal portion 804 of the elongate portion 802 along the longitudinal axis $L_{800}$. In some embodiments, a longitudinal cross section of the spacer 850 can comprise a segment of a circle. In some embodiments, a longitudinal cross section of the spacer 850 can comprise a segment of an oval. For example, a longitudinal cross section of the lateral portions 856a, 856b, 856c, 856d can comprise a segment of a circle or a segment of an oval. The lateral surfaces 862a, 862b, 862c, 862d can comprise a convex curvature. The radius of curvature of the curvature may or may not be uniform.

In some embodiments, a spacer can comprise more or fewer distinct lateral surface portions. One or more lateral surface portions of the plurality of distinct lateral surface portion can curve and/or bow inwardly, for example comprising a concave curvature. The curvature in the one or more lateral surface portions can reduce friction between the spacer and a delivery catheter lumen wall so as to facilitate insertion and/or retraction of the spacer. One or more lateral surface portions of the plurality of distinct lateral surface portion can be parallel or substantially parallel to a longitudinal axis of an associated puncture needle. In some embodiments, the spacer can be asymmetrical around an axis coaxial with the longitudinal axis of the puncture needle. In some embodiments, a shape of the spacer can be predetermined based on an anticipated direction and/or degree of one or more bends in the delivery catheter lumen, including an anticipated direction and/or degree of a sharpest bend.

As described herein, a spacer can be adjacent to a puncture component or a predetermined distance proximal of the puncture component. For example, the spacers 250, 350, 450, 550, 650, 750, 850 described with reference to FIGS. 4 through 10, can be adjacent to or a predetermined distance proximal of the respective puncture component 206, 306, 406, 506, 606, 706, 806. The distal end 254, 354, 454, 554, 654, 754, 854 of the respective spacer 206, 306, 406, 506, 606, 706, 806 can be adjacent to or a predetermined distance proximal of a respective proximal end 208, 308, 408, 508, 608, 708 of the puncture components 206, 306, 406, 506, 606, 706, 806.

In some embodiments, a width and/or a length of the spacers 250, 350, 450, 550, 650, 750, 850 can be predetermined based at least in part on a distance between the spacers 250, 350, 450, 550, 650, 750, 850 and the respective pointed sharp distal end 210, 310, 410, 510, 610, 710, 810 of the puncture components 206, 306, 406, 506, 606, 706, 806. The length can be a longitudinal dimension parallel or substantially parallel to a longitudinal axis of the respective puncture needles 200, 300, 400, 500, 600, 700, 800. The width can be a lateral dimension which is perpendicularly or substantially perpendicularly to the length, such as perpendicular or substantially perpendicular to the longitudinal axes of the puncture needles 200, 300, 400, 500, 600, 700, 800. In some embodiments, the width can be directly related to the distance. In some embodiments, the length can be inversely related to the distance. In some embodiments, the length does not depend on the distance between the spacers 250, 350, 450, 550, 650, 750, 850 and the respective pointed sharp distal end 210, 310, 410, 510, 610, 710, 810 of the puncture components 206, 306, 406, 506, 606, 706, 806.

As shown in FIGS. 4 through 10, the proximal ends 252, 352, 452, 552, 652, 752, 852 and/or the distal ends 254, 354, 454, 554, 654, 754, 854 can be a planar or substantially planar surface. Alternatively, the spacers 250, 350, 450, 550, 650, 750, 850 can comprise a proximal taper or a distal taper, such as a taper from the lateral portion 256, 356, 456, 556, 656, 756, 856 toward the proximal ends 252, 352, 452, 552, 652, 752, 852 and/or the distal ends 254, 354, 454, 554, 654, 754, 854, respectively. A taper may include a curved and/or a linear taper. The spacers 250, 350, 450, 550, 650, 750, 850 can comprise a proximal taper and/or a distal taper to facilitate retraction and/or insertion of the spacers 250, 350, 450, 550, 650, 750, 850 through the delivery catheter lumen.

In some embodiments, the spacers 250, 350, 450, 550, 650, 750, 850 can serve as a dilator configured to be inserted into the opening formed at a target tissue site to enlarge the opening. In some embodiments, the width of the spacers 250, 350, 450, 550, 650, 750, 850 can be selected based at least in part on a desired dilation of the opening. In some embodiments, the spacers 250, 350, 450, 550, 650, 750, 850 can comprise a distal taper to facilitate insertion of the spacers 250, 350, 450, 550, 650, 750, 850 into the opening. In some embodiments, the distal ends 254, 354, 454, 554, 654, 754, 854 can be planar or substantially planar to prevent or reduce insertion of the spacers 250, 350, 450, 550, 650, 750, 850 into the opening.

Figure 11:
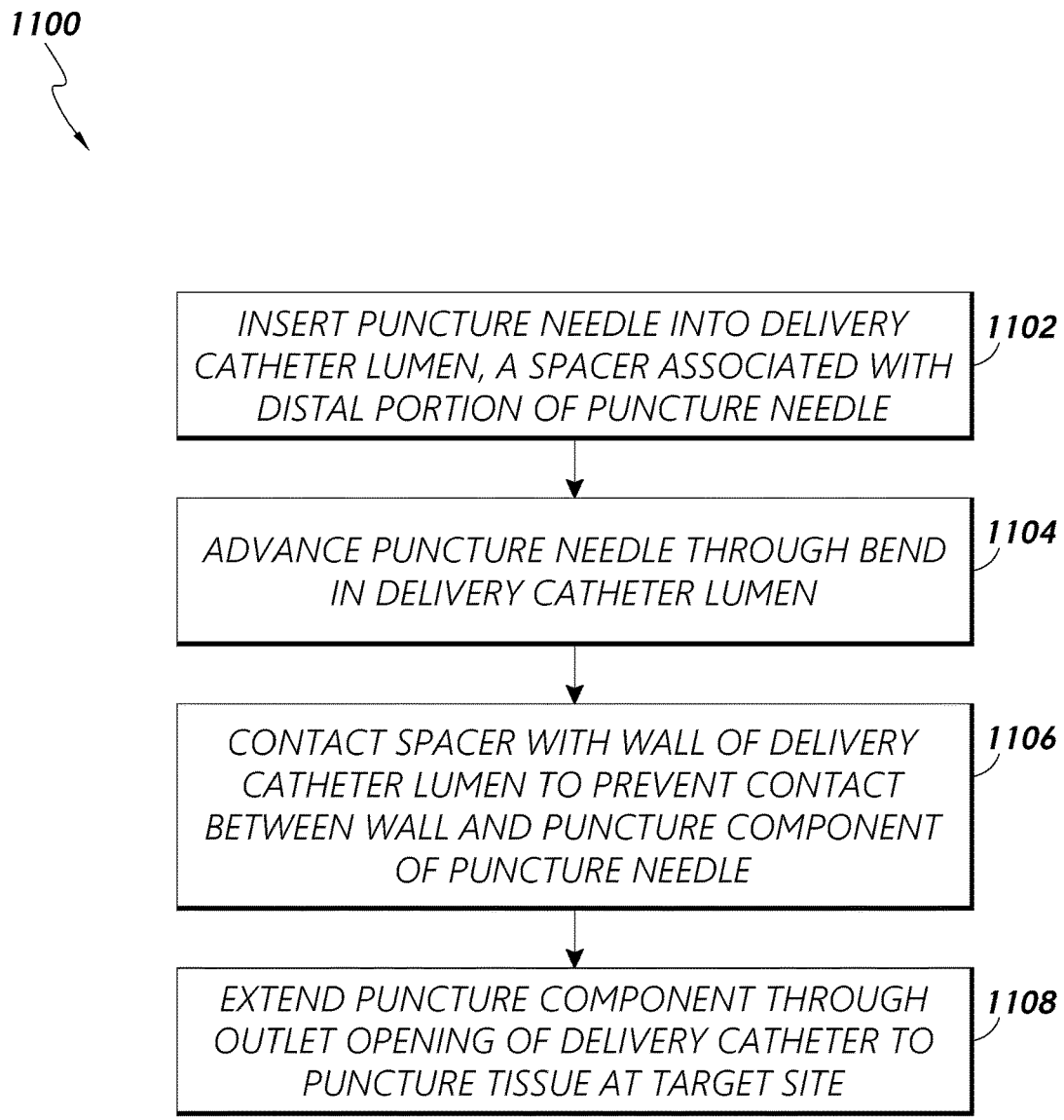
FIG. 11 is a flow diagram of an example of a process for deploying a puncture needle comprising a spacer as described herein.

FIG. 11 is a flow diagram of an example of a process 1100 for deploying a puncture needle comprising a spacer as described herein. In block 1102, the process 1100 involves inserting the puncture needle and an associated spacer into a delivery catheter lumen. The puncture needle can comprise an elongate portion and the spacer can be positioned on a distal portion of the elongate portion. The puncture component can comprise a pointed sharp distal end which can become lodged within a wall of the delivery catheter lumen if the sharp distal end comes into contact with the wall of the delivery catheter lumen.

In block 1104, the process 1100 involves advancing the puncture needle through a bend in the delivery catheter lumen. For example, the puncture component can be inserted through a bend in the delivery catheter lumen without the puncture component becoming jammed within the delivery catheter lumen. In block 1106, the process 1100 involves contacting the spacer with a wall of the delivery catheter lumen so as to prevent contact between the wall and the puncture component of the puncture needle. The spacer can contact the wall to provide space between the delivery catheter lumen wall and the pointed sharp distal end of the puncture component such that the pointed sharp distal end does not contact the wall.

In block 1108, the process 1100 involves extending the puncture component through an outlet opening of the delivery catheter to puncture tissue at a target site. The target tissue site can be at a target site on any number of internal vessels, channels, organs and/or chambers. In some embodiments, the target site can be on a left atrial wall. In some embodiments, the puncture needle can be positioned within a coronary sinus to enable accessing the left atrial wall from within the coronary sinus. For example, a transfemoral approach can be used to position the delivery catheter into the coronary sinus from the right atrium via the coronary sinus ostium. The puncture needle can then be deployed from the delivery catheter lumen to form an opening on the left atrial wall from within the coronary sinus. In some embodiments, a trans-subclavian or a transjugular approach can be used.

In some embodiments, after the opening is formed, at least a portion of the spacer can be optionally inserted into the opening to enlarge the opening. As described herein, in some embodiments, a width the spacer can be selected based on a desired enlargement of the opening formed in the tissue. In some embodiments, the spacer can be configured to reduce or eliminate insertion into the opening in the target tissue.

As described herein, although the spacer is described as being associated with an elongate portion of a puncture needle, in some embodiments, the spacer can instead be associated with a distal exterior portion of a puncture needle sheath configured to receive the puncture needle. The spacer can be on an exterior portion of the puncture needle sheath, such as a distal exterior portion. After the puncture needle sheath and the puncture needle are positioned at a desired position relative to the target tissue site, the puncture needle sheath can be retracted and/or the puncture needle can be advanced to deploy the puncture needle for piercing the target tissue.

Figure 12:
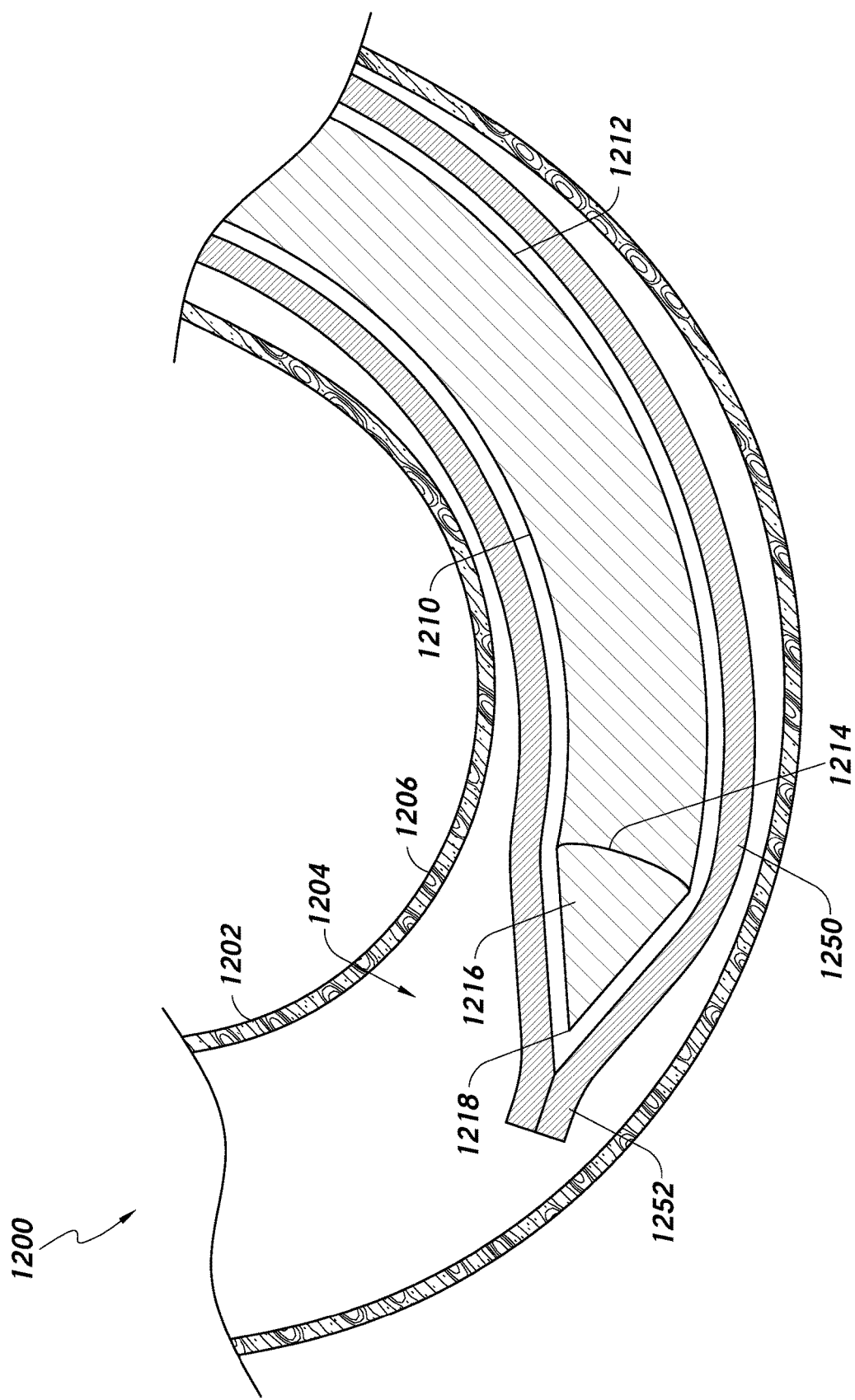
FIG. 12 is a longitudinal cross-sectional view of an example of a puncture needle system comprising a protective cover for a distal end of the puncture needle.

FIG. 12 is a longitudinal cross-sectional view of an example of a puncture needle system 1200. The puncture needle system 1200 can include a puncture needle 1210 and a protective cover 1250 over the puncture needle 1210. FIG. 12 shows the puncture needle system 1200 positioned within a lumen 1204 of a delivery catheter 1202. The puncture needle 1210 can comprise an elongate portion 1212 and a puncture component 1216 at a distal end 1214 of the elongate portion 1212. The puncture component 1216 can have a pointed sharp distal end 1218 and the protective cover 1250 can extend over the pointed sharp distal end 1218 such that the pointed sharp distal end 1218 can be prevented from contacting a wall 1206 of the delivery catheter lumen 1204. For example, the protective cover 1250, such as a distal portion 1252 of the protective cover 1250, can be maintained over the pointed sharp distal end 1218 while the puncture needle 1210 is advanced through any bends in the delivery catheter lumen 1204 such that the pointed sharp distal end 1218 does not contact the wall 1206.

The protective cover 1250 can extend over at least a portion of the puncture needle 1210, including over the puncture component 1216. The delivery catheter 1202 can be positioned at a desired location. Subsequently, the puncture needle 1210 and the protective cover 1250 can be inserted through the delivery catheter lumen 1204 to position the puncture needle 1210 at or proximate to a target tissue site for forming an opening in the tissue. For example, the puncture component 1216 enclosed within the protective cover 1250 can be advanced through the delivery catheter lumen 1204 until the puncture component 1216 is positioned at or proximate to the target tissue site. After the puncture component 1216 is positioned at or proximate to the target tissue site, the puncture needle 1210 can be translated distally relative to the protective cover 1250 to allow the puncture component 1216 to pierce the distal portion 1252 of the protective cover 1250. The unsheathed puncture component 1216 can be used to pierce target tissue for forming the opening in the target tissue. The puncture component 1216 can be extended further, for example extended through a puncture needle outlet opening of the delivery catheter 1202, such that the puncture component 1216 can be used to puncture tissue at the target site.

FIGS. 13 through 25 show various examples of puncture needles which have a puncture component with a blade edge on a distal edge. The blade edge can be sharp so as to be used to cut through tissue so as to form an opening at a target tissue site. In some embodiments, the blade edge can comprise a convex curvature. The blade edge can be a convexly curved blade edge. The blade edge can include a linear portion between opposing curved corners. As described herein, conventional puncture components typically include a pointed sharp distal end. The pointed sharp distal end of the puncture component can become lodged within a delivery catheter lumen wall when the pointed sharp distal end contacts the wall, such as when the puncture component is advanced through a bend in the delivery catheter lumen. The pointed sharp distal end can prick the delivery catheter lumen wall and stick to the wall, resulting in the puncture needle becoming jammed within the delivery catheter lumen. In contrast, the curvature in the blade edge can prevent the blade edge from becoming stuck against the delivery catheter lumen wall when the blade edge contacts the wall. For example, the convexly curved blade edge and/or the blade edge comprising the linear portion between opposing rounded corners can slide along the wall without sticking to the wall when the blade edge contacts the wall at a bend in the delivery catheter lumen. Puncture needles comprising a blade edge as described herein can thereby be advanceable through one or more bends of a delivery catheter lumen.

Figure 13:
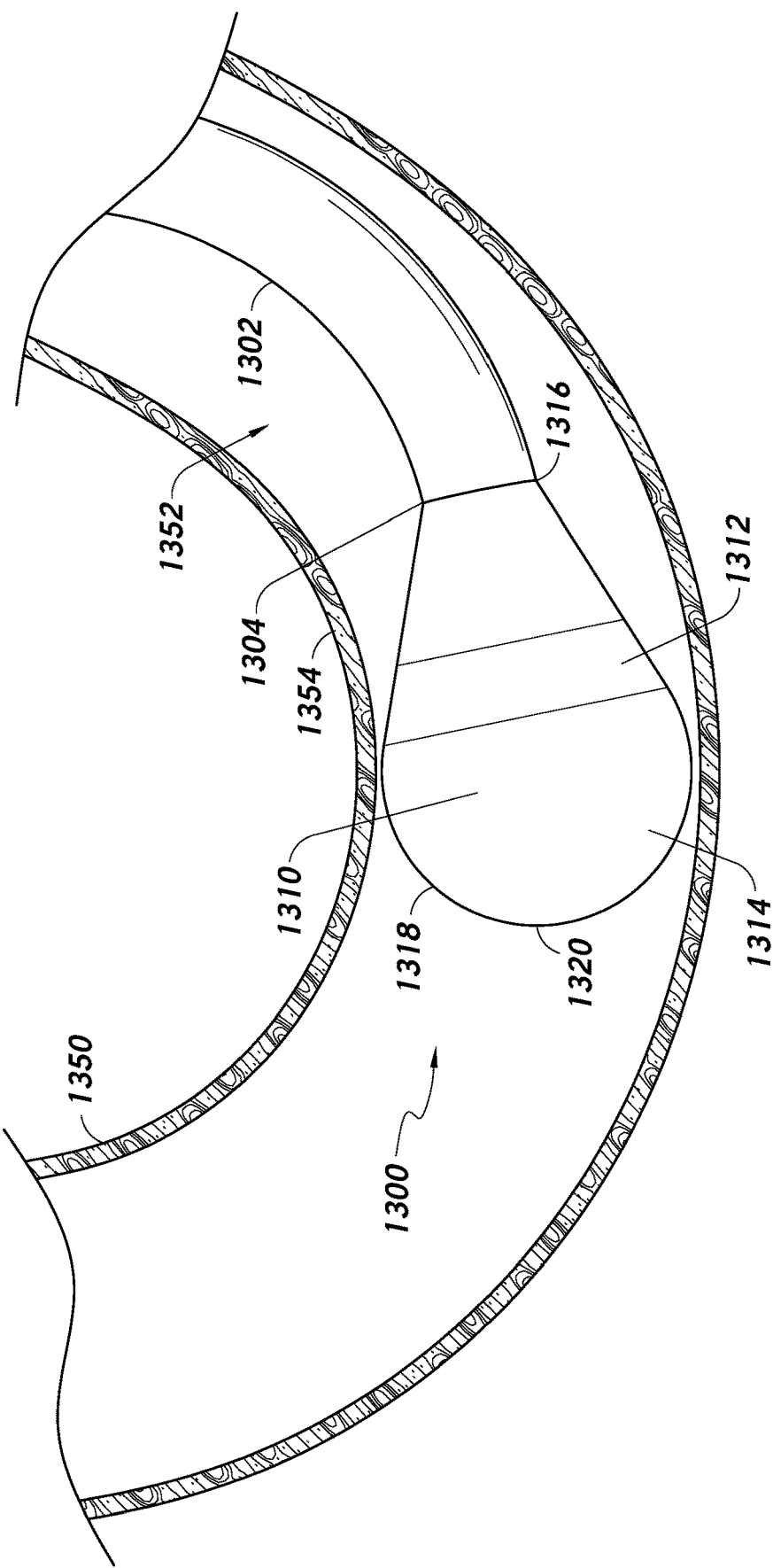
FIG. 13 is a side view of an example of a puncture needle which comprises a puncture component with a curved blade edge positioned within a delivery catheter lumen.

FIG. 13 shows an example of a puncture needle 1300 positioned within a delivery catheter 1350, where the puncture needle 1300 includes a puncture component 1310 with a blade edge 1320. In some embodiments, the puncture component 1310 can comprise a rounded paddle shape, where the blade edge 1320 is on at least a portion of the rounded distal edge of the paddle. The blade edge 1320 can be a sharp edge configured to pierce tissue. The blade edge 1320 can glide along the wall 1354 of the delivery catheter lumen 1352 if the blade edge 1320 contacts the wall 1354, without any portion of the blade edge 1320 becoming lodged within the wall 1354. For example, as the puncture component 1310 is advanced through a bend in the delivery catheter lumen 1354, the blade edge 1320 can come into contact with the delivery catheter lumen wall 1354 without any portion of the blade edge 1320 sticking to the wall 1354. The blade edge 1320 can advantageously facilitate insertion of the puncture needle 1300 through bends in the delivery catheter lumen 1352, without the puncture needle 1300 becoming stuck within the lumen 1352.

Referring to FIG. 13, the puncture needle 1300 can comprise an elongate portion 1302 and the puncture component 1310 can be at a distal end 1304 of the elongate portion 1302. The puncture component 1310 can have a proximal portion 1312 and a distal portion 1314. The proximal portion 1312 can comprise a proximal end 1316 adjacent to the distal end 1304 of the elongate portion 1302. The distal portion 1314 can comprise a distal edge 1318 which includes the blade edge 1320. The distal portion 1314 can comprise a curved edge, such as a convex curve. The distal edge 1318 can comprise the curved edge such that the blade edge 1320 is a curved blade edge. The radius of curvature of the curved edge may or may not be uniform. In some embodiments, the distal portion 1314 can comprise a segment of a circle and/or a segment of an oval. The blade edge 1320 can comprise a segment of a circle and/or a segment of an oval.

Figure 14A:
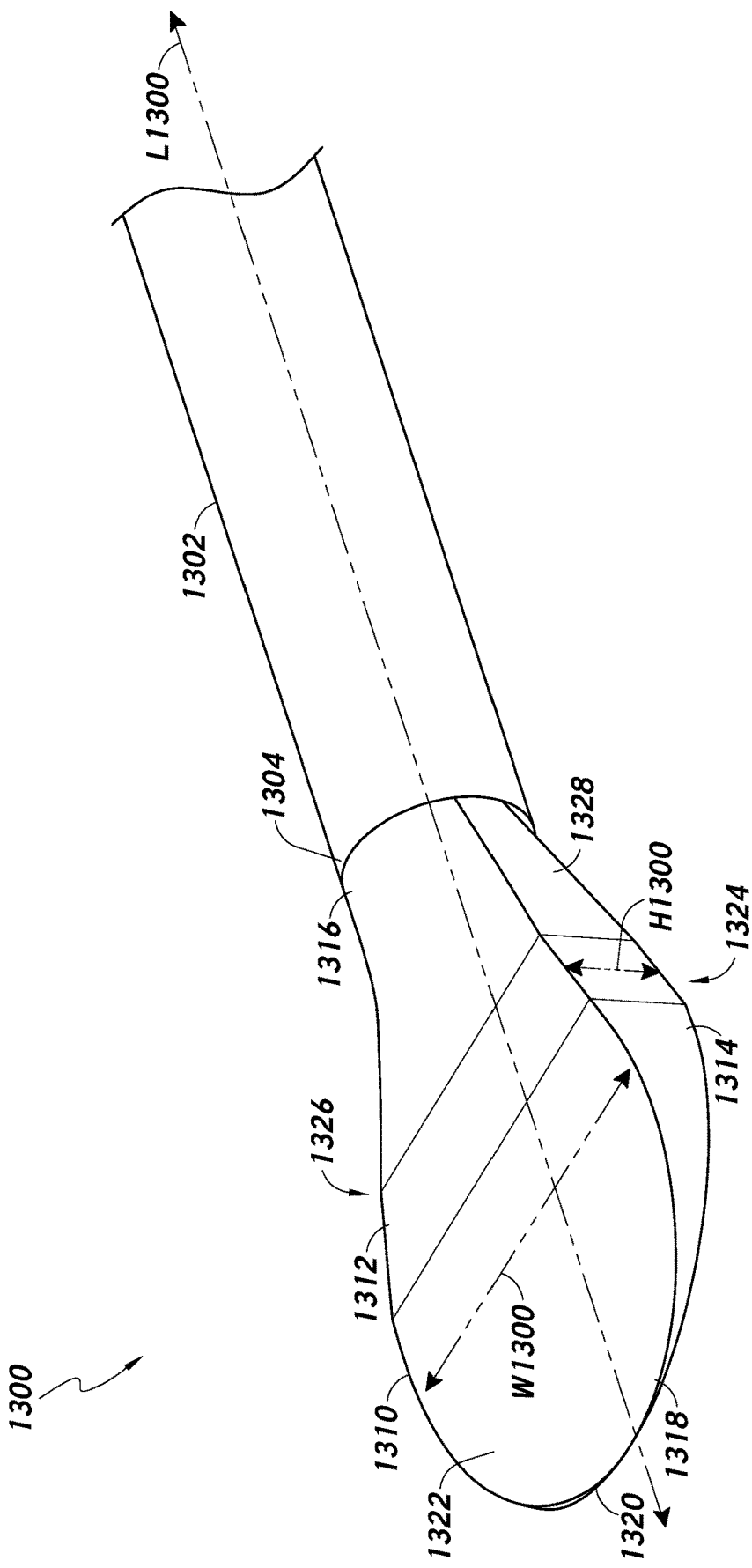

FIG. 14A is a perspective view of the puncture needle 1300. The puncture component 1310 can have two opposing surfaces 1322, 1324 which converge along respective distal edges to form the distal edge 1318. For example, the opposing surfaces 1322, 1324 can be a top surface and a bottom surface, respectively, of the puncture component 1310. The opposing surfaces 1322, 1324 can be planar or substantially planar. In some embodiments, only a portion of the distal edge 1318 comprises the blade edge 1320. For example, a portion of the distal edge 1318 can be blunt. In some embodiments, the blade edge 1320 can extend along the entirety or substantially the entirety of the distal edge 1318. For example, opposing surfaces 1322, 1324 can converge to form the sharp blade edge 1320.

Lateral surfaces 1326, 1328 of the puncture component 1310 can extend between the two opposing surfaces 1322, 1324. In some embodiments, the lateral surfaces 1326, 1328 do not or substantially do not bow and/or curve along a dimension extending between the two opposing surfaces 1322, 1324. A width of the puncture component 1310, such as $W_{1300}$, can be a dimension which extends between respective portions of the lateral surfaces 1326, 1328. The width $W_{1300}$ can be a dimension extending between opposing portions of the lateral surfaces 1326, 1328. For example, a width $W_{1300}$ can extend between a portion of the lateral surface 1326 and a portion of the lateral surface 1328 opposite the portion of the lateral surface 1326. A height of the puncture component 1310, such as $H_{1300}$, can be a dimension extending between respective portions of the opposing surfaces 1322, 1324. The height can be a dimension extending between opposing portions of the surfaces 1322, 1324, between a portion of the top surface 1322 and a portion of the bottom surface 1324 opposite the portion of the top surface 1322. For example, the height can be a dimension perpendicular or substantially perpendicular to a longitudinal axis $L_{1300}$ of the puncture needle 1300. A width can be a dimension perpendicular or substantially perpendicular to both a height and the longitudinal axis $L_{1300}$ of the puncture needle 1300.

FIG. 14B shows a top-down plan view of the puncture needle 1300. FIG. 14C shows a side view of the puncture needle 1300. Referring to FIG. 14B, the proximal portion 1312 can have a width which increases along a direction extending from the proximal end 1316 toward the distal portion 1314. In some embodiments, the top surface 1322 and the bottom surface 1324 can be planar. In some embodiments, the top surface 1322 and the bottom surface 1324 are parallel or substantially parallel to one another. In some embodiments, a cross section of the proximal portion 1312 taken along a plane parallel or substantially parallel to the top surface 1322 or the bottom surface 1324 can comprise a trapezoidal shape. For example, a cross section of the proximal portion 1312 taken along a plane parallel or substantially parallel to the top surface 1322 or the bottom surface 1324 and which includes a portion of the lateral surface 1326 and a portion of the lateral surface 1328 opposite that of the lateral surface 1326 can comprise a trapezoidal shape. The trapezoidal shape can have a pair of opposing parallel sides where a shorter of the parallel sides is positioned proximally and a longer of the parallel sides is positioned distally. A cross section of the distal portion 1314 taken along the same plane can comprise a segment of a circle. For example, the cross section of the distal portion 1314 can comprise a semi-circle, the blade edge 1320 being on at least a portion of the semi-circle. The blade edge 1320 can be on a distal portion of the segment of the circle, and opposing portions of the segment proximal of the blade edge 1320 can be blunt portions. A portion of the puncture component 1310 can comprise an increasing width along a direction extending from the distal edge 1318 toward a proximal portion 1312 so as to facilitate use of the puncture component 1310 as a dilator to enlarge an opening formed using the blade edge 1320.

In some embodiments, the rounded edge of the distal portion 1314, such as the semi-circle shape, can facilitate use of the puncture component 1310 to enlarge the opening formed using the blade edge 1320. The rounded edge can facilitate gradual dilation of the opening. As the enlargement can be performed using one or more blunt portions of the puncture component 1310, atraumatic incremental enlargement can be achieved. For example, enlarging the opening can comprise inserting the blunt portions on the segment of the semi-circle of the distal portion 1314 into the opening to atraumatically enlarge the opening.

In some embodiments, the puncture component 1310 comprising a wider width at a portion proximal of the blade edge 1320 can reduce or prevent contact between the blade edge 1320 and a wall of a delivery catheter lumen. For example, the lateral surfaces 1326, 1328 can contact the wall such that desired space can be maintained between the wall and the sharp blade edge 1320.

Referring to FIG. 14C, the proximal portion 1312 can comprise a portion having a uniform or substantially uniform height. In some embodiments, a cross section of the proximal portion 1312 taken along a plane perpendicular or substantially perpendicular to the top surface 1322 or the bottom surface 1324 can comprise a rectangular shape. For example, a cross section of the proximal portion 1312 taken along a plane which includes opposing portions of the top surface 1326 and bottom surface 1328, a portion of the top surface 1326 and a portion of the bottom surface 1328 opposite that of the top surface 1326, and which extends along a direction extending from the proximal end 1316 to the distal portion 1314, can comprise a rectangular shape. The distal portion 1314 can have a height which decreases along a direction extending from the proximal portion 1312 to the distal edge 1318. For example, a cross section of the distal portion 1314 taken along a plane which includes opposing portions of the top surface 1322 and bottom surface 1324, and which extends along a direction extending from the proximal portion 1312 to the distal edge 1318 can comprise a triangular shape.

Figure 15:
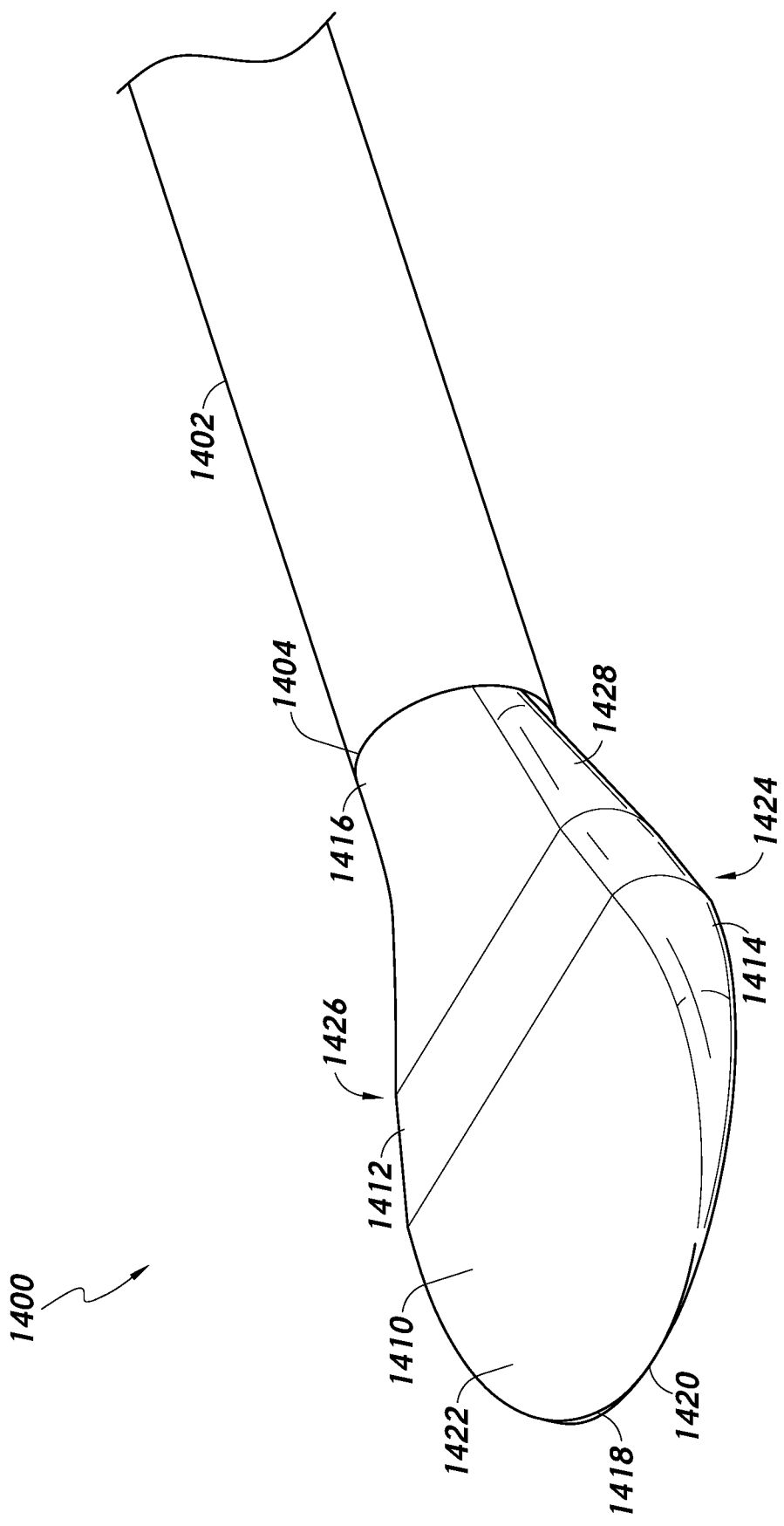
FIG. 15 is a perspective view of an example of a puncture needle comprising a puncture component with a curved blade edge.

FIG. 15 is a perspective view of another example of a puncture needle 1400 which includes a puncture component 1410 with a blade edge 1420. The puncture needle 1400 can have lateral surfaces 1426, 1428 which bow and/or curve outward. Other features of the puncture needle 1400 can be the same as or similar to those of the puncture needle 1300 described with reference to FIGS. 13 and 14. For example, the puncture component 1410 can comprise a rounded paddle shape, where the blade edge 1420 is on at least a portion of the rounded distal edge of the paddle, and where lateral surfaces 1426, 1428 of the puncture component 1410 comprise one or more curvatures. The puncture component 1410 can have a top planar or substantially planar surface 1422 and a bottom planar or substantially planar surface 1424 which converge along respective distal edges to form the distal edge 1418. The blade edge 1420 can be on the distal edge 1418. The blade edge 1420 can extend along the entirety or substantially the entirety of the distal edge 1418, or can extend only along a portion of the distal edge 1418. The lateral surfaces 1426, 1428 can extend between the top surface 1422 and the bottom surface 1424.

A width of the puncture component 1410 can be a dimension which extends between opposing portions of the lateral surfaces 1426, 1428, a portion of the lateral surface 1426 and a portion of the lateral surface 1428 opposite that of the lateral surface 1426. A height of the puncture component 1410 can be a dimension extending between opposing portions of the top surface 1422 and bottom surface 1424, for example, being perpendicular or substantially perpendicular to a longitudinal axis of the puncture needle 1400. The width can be perpendicular or substantially perpendicular to both the height and the longitudinal axis of the puncture needle 1400.

In some embodiments, the top surface 1422 and the bottom surface 1424 can be planar. In some embodiments, the top surface 1422 and the bottom surface 1424 are parallel or substantially parallel to one another. A cross section of the proximal portion 1412 taken along a plane parallel or substantially parallel to the top surface 1422 or the bottom surface 1424 can comprise a trapezoidal shape. For example, a cross section of the proximal portion 1412 taken along a plane parallel or substantially parallel to the top surface 1422 or the bottom surface 1424 and which includes opposing portions of the lateral surfaces 1426, 1428 can comprise a trapezoidal shape. A width of the proximal portion 1412 can increase along a direction extending from the proximal end 1416 toward the distal portion 1414. A cross section of the distal portion 1414 taken along the same plane can comprise a semi-circle, the blade edge 1420 being on at least a portion of the semi-circle. The blade edge 1420 can be a convexly curved blade edge. The proximal portion 1412 can comprise a portion having a uniform or substantially uniform height. For example, a cross section of the proximal portion 1412 taken along a plane which includes opposing portions of the top surface 1426 and bottom surface 1428, and which extends along a direction extending from the proximal end 1416 to the distal portion 1414, can comprise a rectangular shape. The distal portion 1414 can have a height which decreases along a direction extending from the proximal portion 1412 to the distal edge 1418. For example, a cross section of the distal portion 1414 taken along the plane which includes opposing portions of the top surface 1422 and bottom surface 1424, and which extends along a direction extending from the proximal end 1416 to the distal portion 1414, can comprise a triangular shape.

As described herein, the lateral surfaces 1426, 1428 can bow and/or curve outward. Each of the lateral surfaces 1426, 1428 can comprise one or more convex curvatures along a direction extending between the top surface 1422 and the bottom surface 1424, for example perpendicular to or substantially perpendicular to the top surface 1422 and the bottom surface 1424. For example, the lateral surfaces 1426, 1428 can be rounded. The rounded lateral surfaces 1426, 1428 can facilitate insertion and/or retraction of the puncture needle 1400 through a delivery catheter lumen. The one or more curvatures can reduce friction between the puncture component 1410 and the delivery catheter lumen wall. In some embodiments, the rounded lateral surfaces 1426, 1428 can facilitate insertion of the puncture component 1410 into a tissue opening formed using the blade edge 1420 to provide atraumatic enlargement of the opening.

FIGS. 16 through 23 are top-down plan views of additional examples of puncture components which comprise a blade edge. FIGS. 16 to 19 are top-down plan views of some examples of puncture components, or portions thereof, which comprise a curved blade edge. The puncture components 1500, 1600, 1700, 1800 shown in FIGS. 16 to 19 can each have a respective blade edge 1508, 1608, 1708, 1808 which comprises a curve. Each of the puncture components 1500, 1600, 1700, 1800 can have a respective proximal end 1502, 1602, 1702, 1802, and a respective distal edge 1504, 1604, 1704, 1804. In some embodiments, the puncture components 1500, 1600, 1700, 1800, shown can be only a portion of a puncture component, for example the respective proximal ends 1502, 1602, 1702, 1802 being coupled to an intermediate member which is in turn coupled to an elongate portion of a puncture needle. Each of the distal edges 1504, 1604, 1704, 1804 can comprise a curved portion, such as a convex curvature. The curvature can have a uniform or non-uniform radius of curvature. For example, each of the distal edges 1504, 1604, 1704, 1804 can be a convexly curved edge, including a convexly curved edge which comprises a segment of a circle and/or an oval. The blade edges 1508, 1608, 1708, 1808 can be on the respective distal edge 1504, 1604, 1704, 1804. For example, each of the blade edges 1508, 1608, 1708, 1808 can be a convexly curved blade edge, including a blade edge which is a segment of a circle and/or an oval. In some embodiments, the blade edges 1508, 1608, 1708, 1808 can extend along an entirety of a respective distal edge 1504, 1604, 1704, 1804. In some embodiments, the blade edges 1508, 1608, 1708, 1808 can extend along only a portion of the corresponding distal edge 1504, 1604, 1704, 1804. For example, a portion of the distal edges 1504, 1604, 1704, 1804 can be blunt.

A width of a puncture component can increase, decrease or remain the same or substantially the same along a direction extending from a proximal end to a distal edge. Each of the puncture components 1500, 1600, 1700, 1800 can have a respective pair of lateral sides 1506, 1606, 1706, 1806 extending between the corresponding proximal end 1502, 1602, 1702, 1802 and distal edge 1504, 1604, 1704, 1804. The width can be a dimension extending between opposing portions of the lateral sides 1506, 1606, 1706, 1806. A width of the puncture component 1500 can decrease along a direction extending from the distal edge 1504 to the proximal end 1502. A width of the puncture component 1600 can remain the same or substantially the same along at least a portion of a dimension extending from the proximal end 1602 to the distal edge 1604. A width of the puncture components 1700, 1800 can increase along a direction extending from the respective distal edge 1704, 1804 to the respective proximal end 1702, 1802. In some embodiments, the increase width along a direction extending from the respective distal edge 1704, 1804 to the respective proximal end 1702, 1802 can facilitate use of the puncture components 1700, 1800 as a dilator to enlarge an opening formed at a target tissue site.

Referring to FIGS. 16, 17 and 18, the lateral sides 1506, 1606, 1706 can comprise a linear or substantially linear portion. Referring to FIG. 19, the pair of lateral sides 1806 extending between the proximal end 1802 and the distal edge 1804 of the puncture component 1800 can comprise a curvature. For example, the pair of lateral sides 1806 can comprise a convex curvature. As shown in FIG. 16, in some embodiments, the lateral sides 1506 of the puncture component 1500 can meet the distal edge 1504 at rounded corners 1510. The rounded corners 1510 can facilitate insertion of the puncture component 1500 through a delivery catheter lumen. Referring to FIG. 17, the distal edge 1604 can comprise a segment of a circle, such as a semi-circle. For example, the blade edge 1608 can comprise a semi-circle. Referring to FIGS. 18 and 19, the distal edges 1704, 1804 of the puncture components 1700, 1800 can comprise a segment of an oval. For example, the blade edges 1708, 1808 can each comprise a segment of an oval.

FIGS. 20 to 23 are top-down plan views of some examples of puncture components with a blade edge which includes a linear or substantially linear portion between opposing curvatures, such as between opposing rounded corners. The puncture components 1900, 2000, 2100, 2200 shown in FIGS. 20 to 23 can each comprise a respective linear or substantially linear blade edge 1908, 2008, 2108, 2208. Each of the puncture components 1900, 2000, 2100, 2200 can have a respective proximal end 1902, 2002, 2102, 2202, and a respective distal edge 1904, 2004, 2104, 2204. Each of the distal edges 1904, 2004, 2104, 2204 can comprise a linear or substantially linear portion. For example, each of the distal edges 1904, 2004, 2104, 2204 can be linear or substantially linear edges. The blade edges 1908, 2008, 2108, 2208 can each be on the respective distal edge 1904, 2004, 2104, 2204. For example, each of the blade edges 1908, 2008, 2108, 2208 can be a linear or substantially linear blade edge. In some embodiments, the blade edges 1908, 2008, 2108, 2208 can extend along an entirety of respective distal edges 1904, 2004, 2104, 2204, the respective distal edges 1904, 2004, 2104, 2204 being the blade edges 1908, 2008, 2108, 2208.

Figures 20, 21, 22, 23:
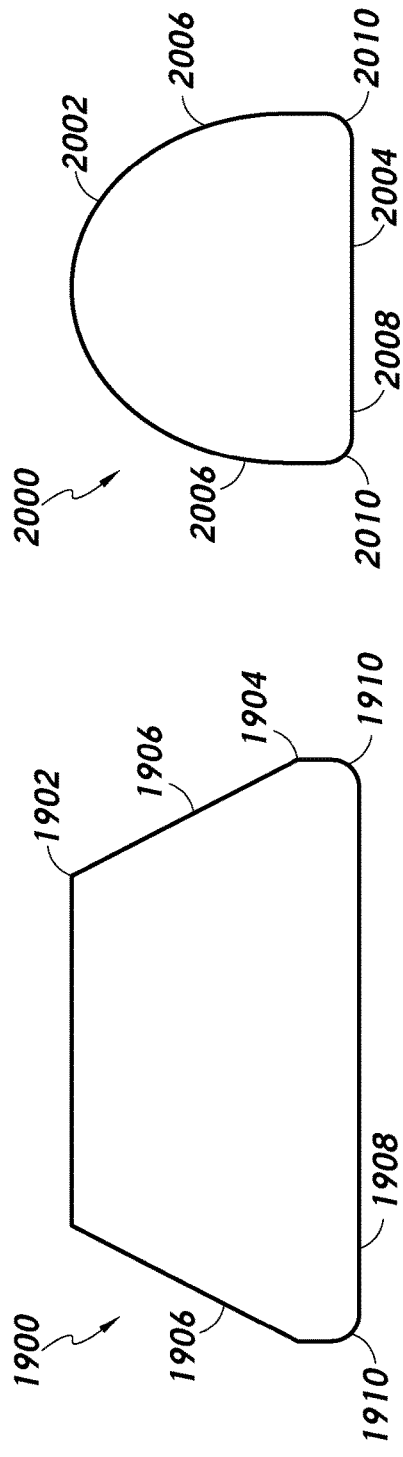
FIGS. 20, 21, 22 and 23 are top-down plan views of examples of puncture components with a blade edge which includes a linear or substantially linear portion extending between curved corners.

Each of the puncture components 1900, 2000, 2100, 2200 can have a pair of respective lateral sides 1906, 2006, 2106, 2206 extending between the respective proximal end 1902, 2002, 2102, 2202, and the respective distal edge 1904, 2004, 2104, 2204. Referring to FIGS. 20, 22 and 23, the lateral sides 1906, 2106, 2206 of the puncture components 1900, 2000, 2100 can each comprise a linear or substantially linear portion. Referring to FIG. 21, the pair of lateral sides 2006 of the puncture component 2000 extending between the proximal end 2002 and the distal edge 2004 can comprise a curvature. For example, the pair of lateral sides 2006 can comprise a convex curvature.

Each of the pairs of lateral sides 1906, 2006, 2106, 2206 can meet the respective distal edges 1904, 2004, 2104, 2204 at rounded corners 1910, 2010, 2110, 2210. In some embodiments, the rounded corners 1910, 2010, 2110, 2210 can be a part of the blade edges 1908, 2008, 2108, 2208. The rounded corners 1910, 2010, 2110, 2210 can be sharp to facilitate tissue puncture at the target site. In some embodiments, the rounded corners 1910, 2010, 2110, 2210 can facilitate insertion of the puncture component 1900, 2000, 2100, 2200 through a delivery catheter lumen, such as to enable gliding of the puncture components 1900, 2000, 2100, 2200 along a wall of the delivery catheter lumen if contact occurs between the puncture components 1900, 2000, 2100, 2200.

A width of a puncture component comprising a linear or substantially linear blade edge can increase, decrease or remain the same or substantially the same along a direction extending from a distal edge to a proximal end. The width can be a dimension extending between opposing portions of the lateral sides 1906, 2006, 2106, 2206. A width of the puncture components 1900, 2000 of FIGS. 20 and 21 can decrease along at least a portion of a dimension extending from the distal edge 1604 to the proximal end 1602. A width of the puncture component 2200 of FIG. 23 can be the same or substantially the same along a direction extending from the distal edge 2204 to the proximal end 2202. A width of the puncture component 2100 of FIG. 22 can increase along a direction extending from the distal edge 2104 to the proximal end 2102. In some embodiments, the increase in width along a direction extending from the distal edge 2104 to the proximal end 2102 can facilitate use of the puncture component 2100 as a dilator to enlarge an opening formed at a target tissue site.

Figure 24:
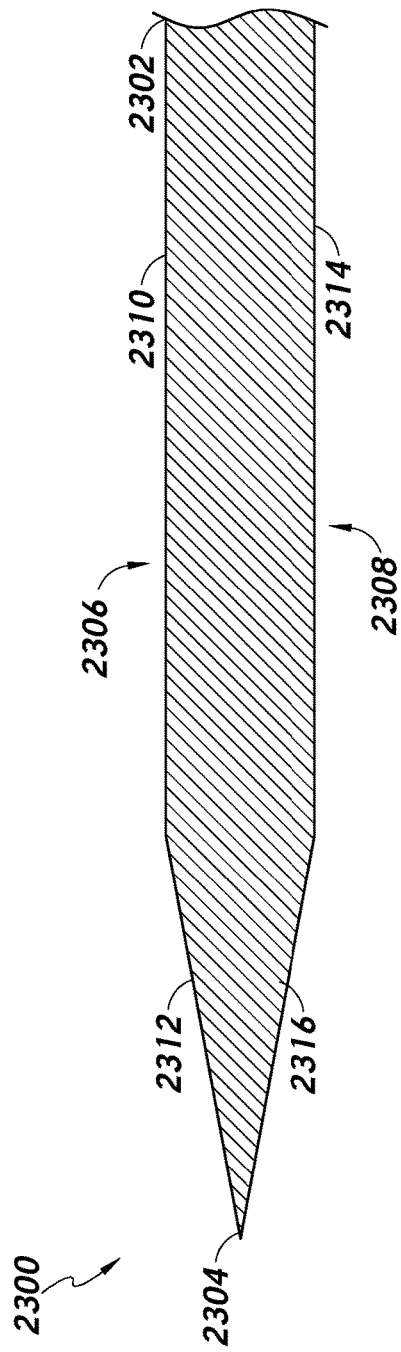
FIGS. 24 and 25 are longitudinal cross-sectional views of examples of puncture components comprising a blade edge.
Figure 25:
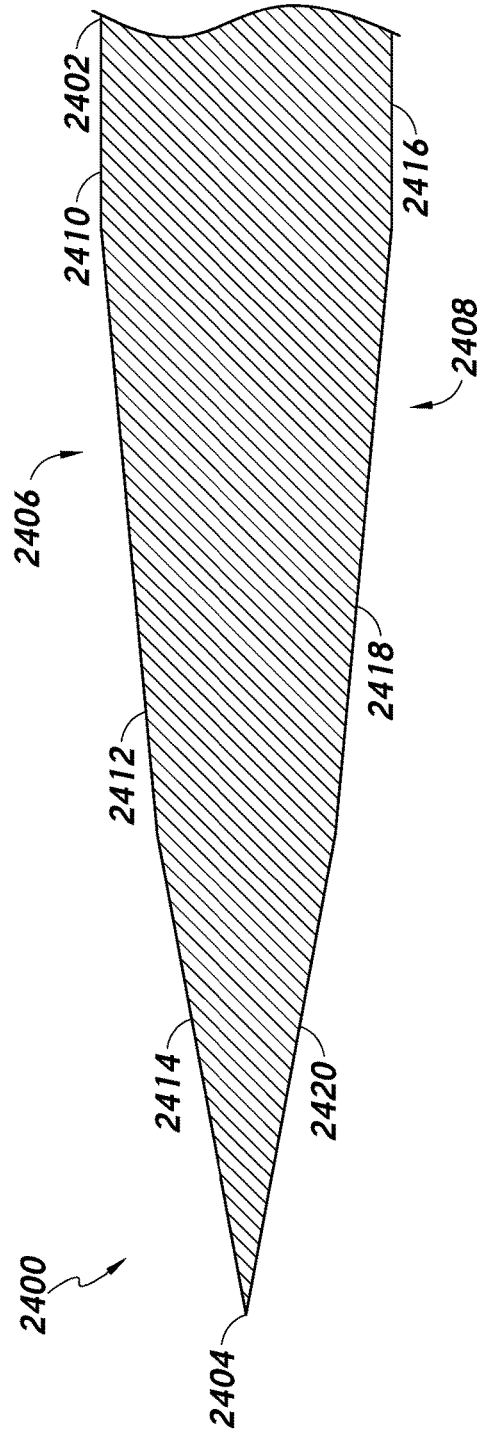

FIGS. 24 and 25 are longitudinal cross-sectional views of examples of puncture components 2300, 2400, respectively. The puncture components 2300, 2400 can comprise respective proximal ends 2302, 2402 and respective distal ends 2304, 2404. Two opposing surfaces can extend between the ends. For example, a first top surface 2306 and a first bottom surface 2308 can extend between the proximal end 2302 and the distal end 2304. A second top surface 2406 and a second bottom surface 2408 can extend between the proximal end 2402 and the distal end 2404.

The top surfaces 2306, 2406 and the bottom surfaces 2308, 2408 can meet along respective distal edges which include the distal ends 2304, 2404. The blade edges of the puncture components 2300, 2400 can be a part of the distal edges. For example, the blade edges can extend into and/or out of the page on which FIGS. 23 and 24 are shown.

The top surfaces 2306, 2406 and the bottom surfaces 2308, 2408 can have one or more opposing portions which slope toward one another. Referring to FIG. 23, the first top surface 2306 can comprise a proximal portion 2310 which is parallel or substantially parallel to an opposing portion of the first bottom surface 2308, such as a proximal portion 2314 of the first bottom surface 2308. The first top surface 2306 can comprise a first top distal portion 2312 and the first bottom surface 2308 can comprise a first bottom distal portion 2316. The first top distal portion 2312 and the first bottom distal portion 2316 can slope toward one another in a direction extending from the first proximal end 2302 to the first distal end 2304. The first top distal portion 2312 and the first bottom distal portion 2316 can slope toward one another and meet at the first distal end 2304. A slope of the first top distal portion 2312 and a slope of the first bottom distal portion 2316 can be the same or different. For example, the first top distal portion 2312 and the first bottom distal portion 2316 can slope toward one another to form the distal edge which includes the blade edge of the puncture component 2300. A slope of the first top distal portion 2312 and a slope of the first bottom distal portion 2316 can be the same or different.

Referring to FIG. 25, the second top surface 2406 can comprise a second top proximal portion 2410 which is parallel or substantially parallel to an opposing portion of the second bottom surface 2408, such as the second bottom proximal portion 2416. The second top surface 2406 can comprise a second top central portion 2412 and a second top distal portion 2414. The second bottom surface 2408 can comprise a second bottom central portion 2418 and a second bottom distal portion 2420. The second top central portion 2412 and the second bottom central portion 2418 can slope toward one another in a direction extending from the second proximal end 2402 to the second distal end 2404. A slope of the second top central portion 2412 and a slope of the second bottom central portion 2414 can be the same or different. The second top distal portion 2414 and the second bottom distal portion 2418 can slope toward one another in a direction extending from the second proximal end 2402 to the second distal end 2404. The second top distal portion 2414 and the second bottom distal portion 2418 can slope toward one another and meet at the second distal end 2404. For example, the second top distal portion 2414 and the second bottom distal portion 2418 can slope toward one another to form the distal edge which includes the blade edge of the puncture component 2400. A slope of the second top distal portion 2416 and a slope of the second bottom distal portion 2418 can be the same or different. A slope of the second top central portion 2412 can be different from that of the second top distal portion 2414. A slope of the second bottom central portion 2418 can be different from that of the second bottom distal portion 2420.

As described herein, in some embodiments, one or more portions of a puncture component can be inserted into a tissue opening to enlarge the opening formed in the tissue. For example, a height, a width and/or a degree of taper of one or both of the puncture components 2300, 2400 can be selected based on a desired enlargement of the opening. A height can be a dimension extending between a portion of the top surfaces 2306, 2406 and a portion of the respective bottom surfaces 2308, 2408 opposite that of the top surfaces 2306, 2406. A width can be a dimension perpendicular or substantially perpendicular to the height, for example extending into and/or out of the page.

In some embodiments, the top surfaces 2306, 2406 and the bottom surfaces 2308, 2408 can be planar or substantially planar. In some embodiments, the top surfaces 2306, 2406 and the bottom surfaces 2308, 2408 can comprise one or more curvatures, including a convex curvature. For example, the puncture components 2300, 2400 can comprise a generally conical shape.

Figure 26:
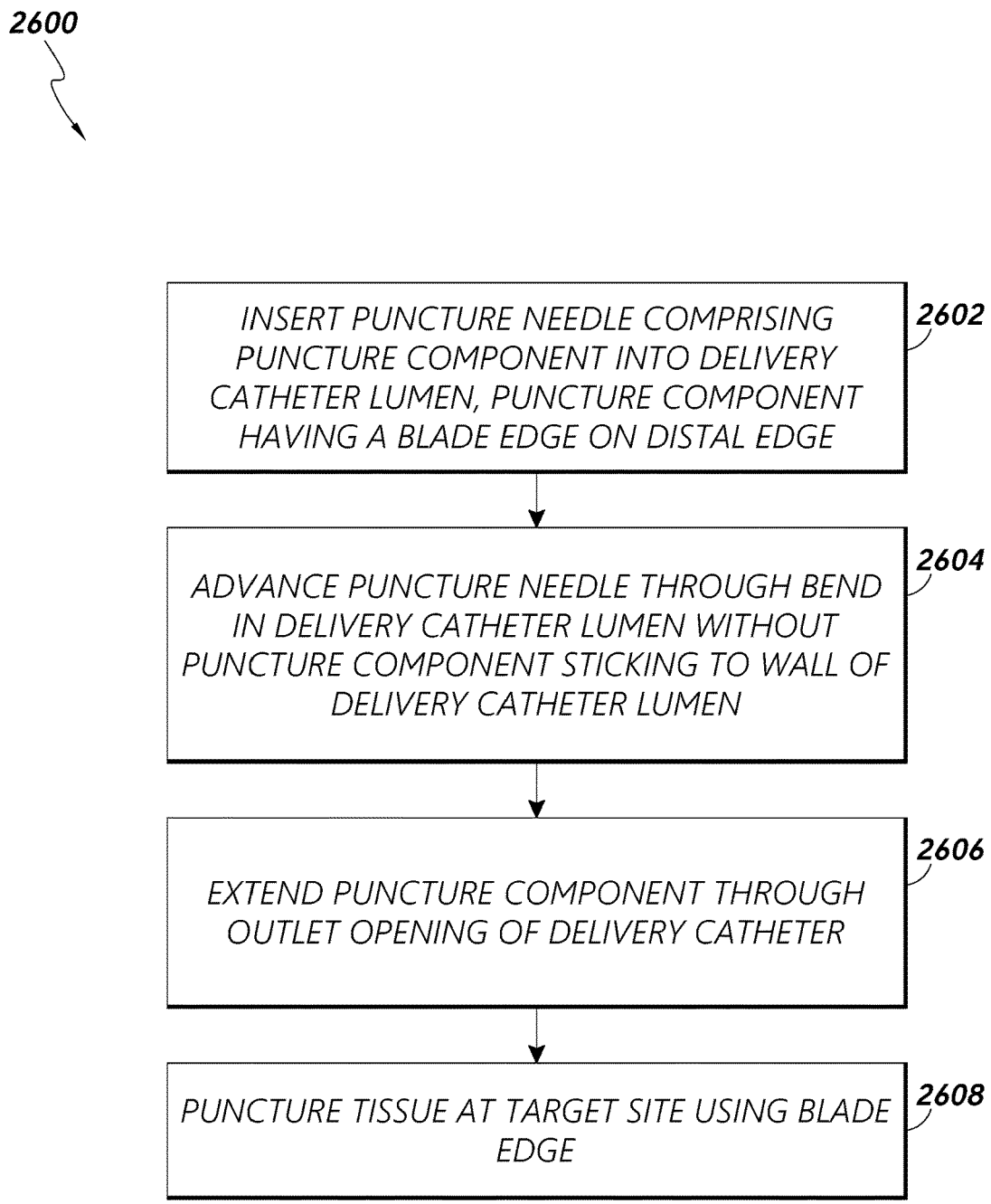
FIG. 26 is a flow diagram of an example of a process for deploying a puncture needle which has a puncture component with a blade edge as described herein.

FIG. 26 is a process flow diagram of an example of a process 2600 for deploying a puncture needle comprising a puncture component with a blade edge as described herein. In block 2602, the process 2600 involves inserting a puncture needle into a delivery catheter lumen. The puncture needle can include a puncture component which has a blade edge configured for piercing tissue. The blade edge can have any one of the configurations as described herein. In some embodiments, the blade edge can be a convexly curved blade edge. In some embodiments, the blade edge can include a linear or substantially linear blade edge between opposing curved corners.

In block 2604, the process 2600 involves advancing the puncture needle through a bend in the delivery catheter lumen. The puncture component can be advanced through the bend without sticking to a wall of the delivery catheter lumen. For example, the blade edge can facilitate sliding of the puncture component along the wall of the delivery catheter lumen. In some embodiments, a portion of the puncture component proximal of the blade edge can have a width wider than a width of the blade edge to facilitate maintaining a desired space between the blade edge and the wall of the delivery catheter lumen, so as to reduce or avoid contact between the blade edge and the wall.

In block 2606, the process 2600 involves extending the puncture component through an outlet opening of the delivery catheter. After the puncture needle is advanced to a desired location, the puncture component can be deployed. In block 2608, the process 2600 involves using the blade edge to puncture tissue at a target tissue site to form an opening in the tissue. As described herein, the target tissue site can be at a target site on any number of internal vessels, channels, organs and/or chambers. In some embodiments, the target site can be on a left atrial wall. In some embodiments, the puncture needle can be positioned within a coronary sinus to enable accessing the left atrial wall from within the coronary sinus. For example, a transfemoral approach can be used to position the delivery catheter into the coronary sinus from the right atrium via the coronary sinus ostium. The puncture needle can then be deployed from the delivery catheter lumen to form an opening on the left atrial wall from within the coronary sinus. In some embodiments, a trans-subclavian or a transjugular approach can be used.

In some embodiments, after the opening is formed, the puncture component comprising the blade edge can be optionally inserted further into the opening to enlarge the opening. As described herein, a dimension and/or a shape of the puncture component can be selected based on a desired enlargement of the opening formed in the tissue. For example, a width of the puncture component can increase along a direction extending from the blade edge toward a proximal portion of the puncture component to facilitate enlargement of the opening. As described herein, gradual dilation can be achieved using, for example, puncture components comprising a rounded shape. As the enlargement can be performed using one or more blunt portions of the puncture component, atraumatic incremental enlargement can also be achieved.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to".

What is claimed is:

1. A puncture needle comprising:
an elongate portion; and
a puncture component associated with a distal end of the elongate portion, the puncture component comprising a proximal portion, an intermediate portion, and a distal portion, the distal portion comprising a distal edge, the distal edge forming a semi-circle, the semi-circle comprising a central blade edge, opposing portions of the semi-circle proximal to the blade edge being blunt, the proximal portion and the distal portion having a height that tapers and the intermediate portion having a constant height, and the blade edge being configured to puncture tissue at a target site; and
wherein the puncture component is configured to be advanced through a lumen of a delivery catheter without the blade edge sticking to a wall of the lumen at a bend in the delivery catheter.

2. The puncture needle of claim 1, wherein the proximal portion of the puncture component has a width narrower than a width of the blade edge.

3. The puncture needle of claim 1, wherein the proximal portion of the puncture component has a width the same as a width of the blade edge.

4. The puncture needle of claim 1, wherein the proximal portion of the puncture component has a height larger than that of the distal portion of the puncture component.

5. A puncture needle comprising:
an elongate portion; and
a puncture component coupled to a distal end of the elongate portion, the puncture component having a top planar surface and a bottom opposing planar surface and lateral surfaces extending between respective edges of the top and bottom opposing planar surfaces, and the puncture component comprising:
a proximal portion, a cross section of the proximal portion taken along a plane including opposing portions of the lateral surfaces comprising a trapezoidal shape, a proximal parallel side of the trapezoidal shape being shorter than a distal parallel side of the trapezoidal shape; and
a distal portion, wherein corresponding portions of the top planar surface and bottom opposing planar surface of the distal portion are converging along respective distal edges to form a convexly curved distal edge, the convexly curved distal edge comprising a blade edge, the blade edge is on a distal portion of the convexly curved distal edge, and opposing portions of the convexly curved distal edge proximal of the blade edge being blunt portions.

6. The puncture needle of claim 5, wherein a width of the proximal portion increases along a direction extending from a proximal end of the puncture component toward the distal portion.

7. The puncture needle of claim 5, wherein the lateral surfaces do not comprise a bow along a dimension extending between the top and bottom opposing planar surfaces.

8. The puncture needle of claim 5, wherein the blade edge comprises a segment of an oval.

9. The puncture needle of claim 5, wherein the blade edge comprises a segment of a circle.

10. The puncture needle of claim 9, wherein the blade edge comprises a semi-circle.

11. The puncture needle of claim 5, wherein the proximal portion comprises a uniform thickness.

* * * * *